US007745023B2

(12) United States Patent
Flickinger et al.

(10) Patent No.: US 7,745,023 B2
(45) Date of Patent: Jun. 29, 2010

(54) STRUCTURED MATERIAL FOR THE PRODUCTION OF HYDROGEN

(75) Inventors: Michael C. Flickinger, Roseville, MN (US); Caroline S. Harwood, Seattle, WA (US); Federico Rey, Coralville, IA (US)

(73) Assignee: Regents of the University of Minnesota, St. Paul, MN (US)

( * ) Notice: Subject to any disclaimer, the term of this patent is extended or adjusted under 35 U.S.C. 154(b) by 1028 days.

(21) Appl. No.: 10/915,934

(22) Filed: Aug. 9, 2004

(65) Prior Publication Data

US 2005/0176131 A1 Aug. 11, 2005

Related U.S. Application Data

(60) Provisional application No. 60/493,745, filed on Aug. 8, 2003.

(51) Int. Cl.
*H01M 8/16* (2006.01)
*H01M 8/18* (2006.01)
(52) U.S. Cl. ............................................ 429/2; 429/19
(58) Field of Classification Search ................ 429/2, 429/19
See application file for complete search history.

(56) References Cited

U.S. PATENT DOCUMENTS

| | | | |
|---|---|---|---|
| 3,992,158 A | 11/1976 | Przybylowicz et al. | |
| 4,050,898 A | 9/1977 | Goffe et al. | |
| 4,427,836 A | 1/1984 | Kowalski et al. | |
| 4,444,879 A | 4/1984 | Foster et al. | |
| 4,791,151 A | 12/1988 | Kowalski et al. | |
| 4,797,363 A | 1/1989 | Teodorescu et al. | |
| 5,026,641 A | 6/1991 | Ishizaki | |
| 5,369,163 A | 11/1994 | Chiou et al. | |
| 5,447,836 A | 9/1995 | Wolber et al. | |
| 5,498,525 A | 3/1996 | Rees et al. | |
| 5,571,722 A | 11/1996 | Rosson | |
| 5,612,184 A | 3/1997 | Rosson | |
| 5,723,330 A | 3/1998 | Rees et al. | |
| 5,728,350 A | 3/1998 | Kinoshita et al. | |
| 5,751,629 A | 5/1998 | Nova et al. | |
| 5,763,170 A | 6/1998 | Raybuck | |
| 5,776,681 A | 7/1998 | Virta et al. | |
| 5,804,083 A | 9/1998 | Ishii et al. | |
| 5,855,836 A | 1/1999 | Leyden et al. | |
| 5,879,951 A | 3/1999 | Sy | |
| 5,925,511 A | 7/1999 | Fuhr et al. | |
| 5,927,547 A | 7/1999 | Papen et al. | |
| 6,079,283 A | 6/2000 | Papen et al. | |
| 6,083,762 A | 7/2000 | Papen et al. | |
| 6,094,966 A | 8/2000 | Papen et al. | |
| 6,475,808 B1 | 11/2002 | Wagner et al. | |
| 6,750,050 B2 | 6/2004 | Gebhard et al. | |
| 7,132,247 B1* | 11/2006 | Lyngberg et al. | 435/7.2 |
| 7,258,938 B2* | 8/2007 | Yamamoto et al. | 429/19 |
| 2001/0041339 A1 | 11/2001 | Anderson et al. | |
| 2002/0127440 A1* | 9/2002 | Yamamoto et al. | 429/2 |

FOREIGN PATENT DOCUMENTS

| | | |
|---|---|---|
| EP | 0 168 933 A2 | 1/1986 |
| EP | 0 314 338 A1 | 5/1989 |
| EP | 0 318 452 A1 | 5/1989 |
| EP | 0 288 203 B1 | 6/1995 |
| EP | 0 469 021 B1 | 11/1995 |
| EP | 0 711 199 B1 | 3/1999 |
| JP | 62138502 | 6/1987 |
| JP | 62294083 | 12/1987 |
| WO | WO 89/03878 A1 | 5/1989 |
| WO | WO 90/04037 | 4/1990 |
| WO | WO 90/04041 A1 | 4/1990 |
| WO | WO 90/05910 A1 | 5/1990 |
| WO | WO 90/08836 A1 | 8/1990 |
| WO | WO 90/12887 A1 | 11/1990 |
| WO | WO 92/15687 A1 | 9/1992 |
| WO | WO 95/03878 A1 | 2/1995 |
| WO | WO 95/19446 A1 | 7/1995 |
| WO | WO 95/25116 A1 | 9/1995 |
| WO | WO 96/13159 A1 | 5/1996 |
| WO | WO 00/16098 A1 | 3/2000 |

OTHER PUBLICATIONS

Computational Biology at ORNL, "*Rhodopseudomonas palustris* analysis files," Version 1, Retrieved from the Internet: URL:<http://genome.ornl.gov/microbial/rpal>, 1 pg., Aug. 8, 2003.
Oda et al., "Functional Genomic Analysis of Three Nitrogenase Isozymes in the Photosynthetic Bacterium *Rhodopseudomonas palustris*," *J. Bacteriol.*, Nov. 2005; 187(22):7784-7794.
Barbosa et al., "Acetate as a carbon source for hydrogen production by photosynthetic bacteria," *J. Biotechnol.*, 2001;85:25-33.
Better Bacterial Fuel Cell Demoed, Technology Research News, Jul. 30, 2003, issue 25 of Angewandte Chemie, [retrieved on May 5, 2005]. Retrieved from the Internet:<URL:http://matr.net/article-7578.html, 2 pgs.
"Bug Light: 1998 Discover Technology Awards," *Discover*, 1998;19(7):84.
Dischert et al., "The synthesis of *Rhodobacter capsulatus* HupSL hydrogenase is regulated by the two-component HupT/HupR system," *Mol. Microbiol.*, 1999;34(5):995-1006.
Egland et al., "A cluster of bacterial genes for anaerobic benzene ring biodegradation," *Proc. Natl. Acad. Sci. USA*, 1997;94:6484-6489.
Elsen et al., "The *hupTUV* Operon is Involved in Negative Control of Hydrogenase Synthesis of *Rhodobacter capsulatus*," *J. Bacteriol.*, 1996;178(17):5174-5181.

(Continued)

*Primary Examiner*—Suzanne M. Noakes
(74) *Attorney, Agent, or Firm*—Mueting Raasch & Gebhardt, P.A.

(57) ABSTRACT

The present invention provides composite biological devices that include biological material as an integral component thereof. The devices can be used for producing hydrogen gas, for example.

61 Claims, 10 Drawing Sheets

OTHER PUBLICATIONS

Elsen et al., "Purification and In Vitro Phosphorylation of HupT, a Regulatory Protein Controlling Hydrogenase Gene Expression in *Rhodobacter capsulatus,*" *J. Bacteriol.*, 1997;179(3):968-971.

Ferrandez et al., "Cluster II *che* Genes from *Pseudomonas aeruginosa* Are Required for an Optimal Chemotactic Response," *J. Bacteriol.*, 2002;184(16):4374-4383.

Flickinger, Michael C., Biotechnology Development grant (no abstract on file), Grant No. 1T32GM08347-01A1 [online]. National Institutes of General Medical Sciences, project dates Sep. 25, 1990-Jun. 30, 1995 [retrieved on Jan. 24, 2001]. Retrieved from the Internet: URL: http.commons.cit.nih.gov/ crisp_historical/ crisp_lib.getdoc?textkey=3538536 &p_grant_num=1T32GM08347-01A1&p_query=ticket=18343 &p_audit_session_id=334651&p_keywords=>, 1 pg.

Flickinger, Michael C., Biotechnology Development grant (no abstract on file), Grant No. 5T32GM08347-02 [online]. National Institutes of General Medical Sciences, project dates Sep. 25, 1990-Jun. 30, 1995 [retrieved on Jan. 24, 2001]. Retrieved from the Internet: URL: http.commons.cit.nih.gov/crisp_ historical/ crisp_lib.getdoc?textkey=3538537 &p_grant_num=5T32GM08347-02&p_query=ticket=18343 &p_audit_session_id=334651&p_keywords=>, 1 pg.

Flickinger, Michael C., Biotechnology Development grant (no abstract on file), Grant No. 5T32GM08347-03 [online]. National Institutes of General Medical Sciences, project dates Sep. 25, 1990-Jun. 30, 1995 [retrieved on Jan. 24, 2001]. Retrieved from the Internet: URL: http.commons.cit.nih.gov/crisp_historical/ crisp_lib.getdoc?textkey=3538538 &p_grant_num=5T32GM08347-03 &p_query=ticket=18343 &p_audit_session_id=334651&p_keywords=>, 1 pg.

Flickinger, Michael C., Biotechnology Development grant (no abstract on file), Grant No. 5T32GM08347-04 [online]. National Institutes of General Medical Sciences, project dates Sep. 25, 1990-Jun. 30, 1995 [retrieved on Jan. 24, 2001]. Retrieved from the Internet: URL: http.commons.cit.nih.gov/ crisp_historical/ crisp_lib.getdoc?textkey=2167984 &p_grant_num=5T32GM08347-04&p_query=ticket=18343 &p_audit_session_id=334651&p_keywords=>, 1 pg.

Flickinger, Michael C., Biotechnology Development grant (no abstract on file), Grant No. 5T32GM08347-05 [online]. National Institutes of General Medical Sciences, project dates Sep. 25, 1990-Jun. 30, 1995 [retrieved on Jan. 24, 2001]. Retrieved from the Internet: URL: http.commons.cit.nih.gov/ crisp_historical/ crisp_lib.getdoc?textkey=2167985 &p_grant_num=5T32GM08347-05&p_query=ticket=18343 &p_audit_session_id=334651&p_keywords=>, 1 pg.

Flickinger, Michael C. "Enhanced Gene Expression in Immobilized Whole-Cell Biocatalysis," Grant No. 9424063, Continuing Grant, Aug. 1, 1995-Jul. 31, 1998 (abstract) [online]. National Science Foundation, Division of Bioengineering and Environmental Systems, Washington, D.C. [retrieved Jan. 23, 2001]. Retrieved from: Dialog Information Services, FEDRIP Database, 1 pg.

Flickinger, Michael S., 2004-2005, IREE Seed Grant Program, Final Report, "Investigation of Composite Coatings for Photo Biochemical Generation of Hydrogen from Carbohydrates," IREE Project No. Seed Grant SG-H3-2004, [retrieved on Oct. 7, 2005]. Retrieved from the Internet: URL:<64.233.167/ search?q=cache:C8Ay6ws3_L8J:www1.umn.edu/iree/docs/ final_sg_h3_2004.doc+...>, 3 pgs.

Flickinger, Michael C., 2004-2005 IREE Special Opportunity Grant Program, Final Project Report, "Investigation of a Thin, Multi-Layer Latex Coating Photobioreactor for Optimal Light Adsorption and Hydrogen Evolution using Non-Growing *Rhodopseudomonas palustris* Mutants," [retrieved on Aug. 8, 2005]. Retrieved from the Internet: URL:<72.14.207/ search?q=cache:nP7woNXQcqEJ:www1.umn.edu/iree/docs/ so3_2004.doc+%2B...>, 3 pgs.

Flickinger et al., "Photosynthetic Bacterial Paints that Produce Hydrogen," PowerPoint Presentation at Biocycle, Nov. 17-19, 2003, 47 pgs.

Flynn et al., "Accumulation of $O_2$-tolerant phenotypes in $H_2$-producing strains of *Chlamydomonas reinhardtii* by sequential applications of chemical mutagenesis and selection," *Int. Journ. Hydro. Energy*, 2002;27:1421-1430.

Freemantle, "Downsizing Chemistry: Chemical analysis and synthesis on microchips promise a variety of potential benefits," *Chemical and Engineering News*, Feb. 22, 1999;77:27-36.

Hart et al., "On the use of screen- and ink-jet printing to produce amperometric enzyme electrodes for lactate," *Biosensors and Bioelectronics*, 1996;11(3):263-270.

Hart et al., "Recent developments in the design and application of screen-printed electrochemical sensors for biomedical, environmental and industrial analyses," *Trends in Analytical Chemistry*, 1997;16(2):89-103.

Harwood et al., "Mining the *Rhodopseudomonas* Genome for Hydrogen," U.S. Army Research Office Workshop, Apr. 26, 2004, Cashiers, NC, PowerPoint presentation, 20 pgs.

Harwood et al., "Anaerobic and Aerobic Metabolism of Diverse Aromatic Compounds by the Photosynthetic Bacterium *Rhodopseudomonas palustris*," *Appl. Environ. Microbiol.*, 1988;54(3):712-717.

Hellemans, "Rubber Mold Carves a Path to Micromachines," *Science*, 1999;285:19,21.

Hillmer et al., "$H_2$ Metabolism in the Photosynthetic Bacterium *Rhodopseudomonas capsulata*: $H_2$ Production by Growing Cultures," *J. Bacteriol.*, 1977;129(2):724-731.

Ho et al., "Site-directed mutagenesis by overlap extension using the polymerase chain reaction," *Gene*, 1989;77:51-59.

Horton et al., "Engineering hybrid genes without the use of restriction enzymes: gene splicing by overlap extension," *Gene*, 1989;77:61-68.

Huang et al., "Microstructure Evolution in Polymer Latex Coatings for Whole-Cell Biocatalyst Application," *Journal of Colloid and Interface Science*, 1999;215(2):226-243.

Kenis et al., "Microfabrication Inside Capillaries Using Multiphase Laminar Flow Patterning," *Science*, 1999;285:83-85.

Kim et al., "Regulation of benzoate-CoA ligase in *Rhodopseudomonas palustris*," *FEMS Microbiol. Lett.*, 1991;83:199-203.

Kleihues et al., "The $H_2$ Sensor of *Ralstonia eutropha* Is a Member of the Subclass of Regulatory [NiFe] Hydrogenases," *J. Bacteriol.*, 2000;182(10):2716-2724.

Kondo et al., "Hydrogen production by combining two types of photosynthetic bacteria with different characteristics," *Int. J. Hydro. Energy*, 2002;27:1303-1308.

Kumar et al., "Continuous hydrogen production by immobilized *Enterobacter cloacae* IIT-BT 08 using lignocellulosic materials as solid matrices," *Enzyme and Microbial Technology*, 2001;29:280-287.

Larimer et al., "Complete genome sequence of the metabolically versatile photosynthetic bacterium *Rhodopseudomonas palustris*," *Nature Biotechnology*, 2004;22(1):55-61.

Lenz et al., "The Hydrogen-Sensing Apparatus in *Ralstonia eutropha*," *J. Mol. Microbiol. Biotechnol.*, 2002;4(3):255-262.

Lenz et al., "A novel multicomponent regulatory system mediates $H_2$ sensing in *Alcaligenes eutrophus*," *Proc Natl. Acad. Sci. USA*, 1998;95:12474-12479.

Lyngberg, "Patch Coating a Bio-indicator," Abstract and Poster, Coating Process Fundamentals Program—Fall Review, University of Minnesota Center for Interfacial Engineering, NSF Engineering Research Center, Sep. 22, 1997; Web publication Sep. 17, 1997, 17 pgs.

Lyngberg et al., "A Patch Coating Method for Preparing Biocatalytic Films of *Escherichia coli*," Biotechnology and Bioengineering, 1999;62(1):44-55.

Lyngberg et al., "Engineering the Microstructure and Permeability of Thin Multilayer Latex Biocatalytic Coatings Containing *E. coli*," *Biotechnology Progress*, 2001;17:1169-1179.

Lyngberg et al., "Mercury Detection Using Latex Immobilized Cells," Abstract and Poster, North Central Branch American Society of Microbiology, St. Cloud State University, MN, Oct. 1997, 10 pgs.

Lyngberg et al., "A single-use luciferase-based biosensor using copolymer-film immobilized viable *E. coli* HB101,"Abstract, database CHEMABS [Online] Chemical Abstracts Service, Columbus, Ohio, retrieved from STN XP002127579 & Book of Abstracts, 216th ACS National Meeting, Boston, Aug. 23-27, 1998, 1 pg.

Lyngberg et al., "A single-use luciferase-based mercury biosensor using *Escherichia coli* HB101 immobilized in a latex copolymer film,"Abstract, CHEMABS [Online] Chemical Abstracts Service, Columbus, Ohio, retrieved from STN database accession No. 131:268025 XP002127580, 1 pg., 1999.

Lyngberg et al., "A single-use luciferase-based mercury biosensor using *Escherichia coli* HB101 immobilized in a latex copolymer film," *Journal of Industrial Microbiology and Biotechnology*, 1999;23:668-676.

Maniatis et al., *Molecular Cloning: A Laboratory Manual*, Cold Spring Harbor Laboratory Press, Cold Spring Harbor, New York, Title page, publication page and table of contents only, 1982;8 pgs.

Mao et al., "Screening Photosynthetic Bacteria for Hydrogen Production from Organic Acids," *J. Ferment. Technol.*, 1986;64(3):245-249.

Martens et al., "Immobilisation of photosynthetic cells based on film-forming emulsion polymers," *Anal. Chimica Acta*, 1994;292:49-63.

Miyake et al., "Improvement of Bacterial Light-Dependent Hydrogen Production by Altering the Photosynthetic Pigment Ratio," *BioHydrogen*, Zaborsky et al., Eds., New York, NY, 1998:81-86.

Mulchandani et al. "Biosensor for Direct Determination of Organophosphate Nerve Agents Using Recombinant *Escherichia coli* with Surface-Expressed Organophosphorus Hydrolase. 1. Potentiometric Microbial Electrode," *Anal. Chem.*, 1998; 70:4140-4145.

National Center for Biotechnology Information, National Library of Medicine, National Institutes of Health, GenBank Locus BX571963, Accession No. BX571963, "*Rhodopseudomonas palustris* CGA009 complete genome," [online]. Bethesda, MD [retrieved on May 5, 2005]. Retrieved from the Internet:<URL: ncbi.nlm.nih.gov/entrez/viewer.fcgi?db=nucleotide&val=39748133>; 2 pgs.

National Center for Biotechnology Information, National Library of Medicine, National Institutes of Health, GenBank Locus CAE30046, Accession No. CAE30046, "Nitrogenase stabilizer NifW [*Rhodopseudomonas palustris* CGA009]," [online]. Bethesda, MD [retrieved on May 5, 2005]. Retrieved from the Internet:<URL:ncbi.nlm.nih.gov/entrez/viewer.fcgi?db=nucleotide&val=39651523>; 2 pgs.

National Center for Biotechnology Information, National Library of Medicine, National Institutes of Health, GenBank Locus NC_005296, Accession No. NC_005296, "*Rhodopseudomonas palustris* CGA009, complete genome," [online]. Bethesda, MD [retrieved on May 5, 2005]. Retrieved from the Internet:<URL:ncbi.nlm.nih.gov/entrez/viewer.fcgi?db=nucleotide&val=39933080>; 88 pgs.

Oda et al., "Gene Expression Profiles of *Rhodopseudomonas palustris* Nitrogenases by Whole Genome Microarray," DOE Genomes to Life Contractor-Grantee Workshop III, Feb. 6, 2005, Washington, D.C., PowerPoint presentation 21 pgs.

Oda et al., "Gene Expression Profiles of *Rhodopseudomonas palustris* Nitrogenases by Whole Genome Microarray," DOE Genomes to Life Contractor-Grantee Workshop III, Feb. 6, 2005, Washington, D.C., abstract, 1 pg.

Parales et al., "Construction and use of a new broad-host-range lacZ transcriptional fusion vector, pHRP309, for Gram bacteria." *Gene*, 1993;133:23-30.

Pelletier et al., "2-Hydroxycyclohexanecarboxyl Coenzyme A Dehydrogenase, an Enzyme Characteristic of the Anerobic Benzoate Degradation Pathway Used by *Rhodopseudomonas palustris*," *J. Bacter.*, 2000;182(10):2753-2760.

Quandt et al., "Versatile suicide vectors which allow direct selection for gene replacement in Gram-negative bacteria," *Gene*, 1993;127:15-21.

Rey et al., "Hydrogen Production by the Phototrophic Bacterium *Rhodopseudomonas palustris*," Poster presented at Society for Industrial Microbiology, Annual Meeting, Minneapolis, MN, Aug. 10-14, 2003, 2 pgs.

Richaud et al., "Identification and Sequence Analysis of the *hup*R$_1$ Gene, Which Encodes a Response Regulator of the NtrC Family Required for Hydrogenase Expression in *Rhodobacter capsulatus*," *J. Bacteriol.*, 1991;173(18):5928-5932.

Samanta et al., "*Rhodopseudomonas palustris*, a photosynthetic alpha proteobacterium encodes three distinct nitrogenases," 103$^{rd}$ American Society for Microbiology General Meeting; Washington, D.C. May 19-22, 2003, Abstracts of the General Meeting of the American Society for Microbiology, 2003;103:K-068, 1 pg.

Sasikala et al., "Biodegradation and Metabolism of Unusual Carbon Compounds by Anoxygenic Phototrophic Bacteria," *Adv. Microbiol. Physiol.*, 1998;39:339-375.

Selifonova et al., "Bioluminescent Sensors for Detection of Bioavailable Hg(II) in the Environment," *Applied and Environmental Microbiology*, 1993;59(9):3083-3090.

Simon et al., "A Broad Host Range Mobilization System for In Vivo Genetic Engineering: Transposon Mutagenesis In Gram Negative Bacteria," *Bio/Technology*, 1983;1:784-790.

Swope et al., "Activation and Regeneration of Whole Cell Biocatalysts: Initial and Periodic Induction Behavior in Starved *Escherichia coli* after Immobilization in Thin Synthetic Films," *Biotechnology and Bioengineering*, 1996;51:360-370.

Swope et al., "The Use of Confocal Scanning Laser Microscopy and Other Tools to Characterize *Escherichia coli* in a High-Cell-Density Synthetic Biofilm," *Biotechnology and Bioengineering*, 1996;52:340-356.

Swope et al., "Investigation of Gene Expression in Synthetic Biofilms to Extend the Activity of Immobilized Whole Cell Catalysts," *Progress in Biotechnology 11, Immobilized Cells: Basics and Applications*, Proceedings of an International Symposium, The Working Party on Applied Biocatalysis of the European Federation of Biotechnology, The Netherlands, Nov. 26-29, 1995;313-319.

Thiagarajan et al., "Cryo-Electron Microscopy of Polymer Particles in a High Cell Density Synthetic Biofilm," *Progress in Biotechnology 11, Immobilized Cells: Basics and Applications*, Proceedings of an International Symposium, The Working Party on Applied Biocatalysis of the European Federation of Biotechnology, The Netherlands, Nov. 26-29, 1995;298-303.

Thiagarajan et al., "Investigation of Oxygen Consumption by *E. coli* Immobilized in a Synthetic Biofilm Using a Thin Film Plug Reactor (TFPR)," *Progress in Biotechnology 11, Immobilized Cells: Basics and Applications*, Proceedings of an International Symposium, The Working Party on Applied Biocatalysis of the European Federation of Biotechnology, The Netherlands, Nov. 26-29, 1995;304-312.

Thiagarajan et al., "Microstructure of a Biocatalytic Latex Coating Containing Viable *Escherichia coli* Cells," *J. Colloid and Interface Science*, 1999;215:244-257.

Van Soom et al., "HoxA is a transcriptional regulator for expression of the *hup* structural genes in free-living *Bradyrhizobium japonicum*," Mol. Microbiol., 1997;23(5):967-977.

Vasilyeva et al., "Characterization of a Novel Light-Harvesting Mutant of *Rhodobacter sphaeroides* with Relation to Photohydrogen Production," *BioHydrogen*, New York, NY, 1998:123-131.

Vincenzini et al., "Hydrogen Production by Immobilized Cells. I. Light Dependent Dissimilation of Organic Substances by *Rhodopseudomonas Palustris*," *Int. Hydrogen Energy*, 1982;7(3):231-236.

Yanisch-Perron et al., "Improved M13 phage cloning vectors and host strains: nucleotide sequences of the M13mp18 and pUC19 vectors," *Gene*, 1985;33:103-119.

\* cited by examiner

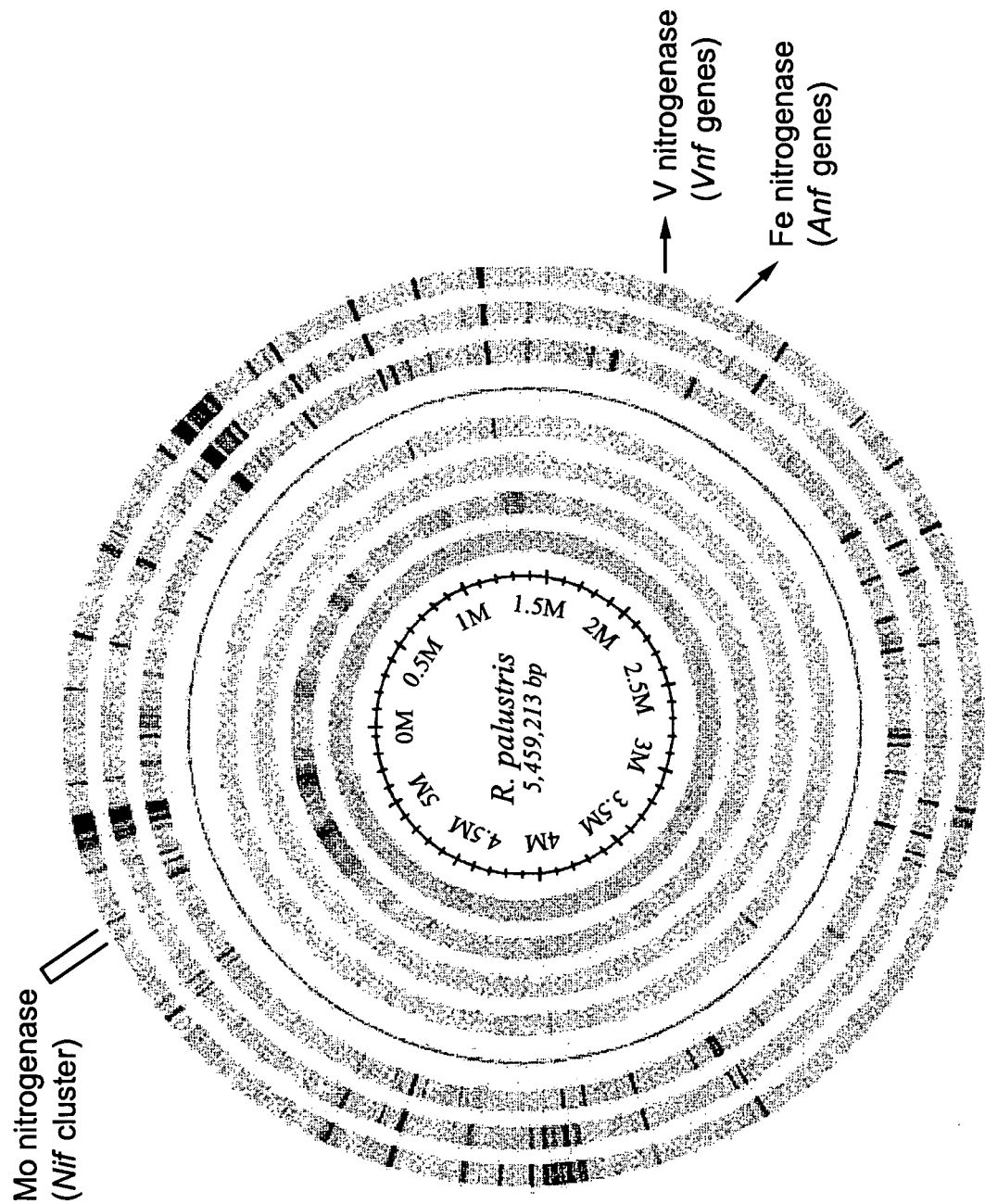
Fig. 2  Rhodopseudomonas Has Three Nitrogen Fixation Gene Clusters

SEQUENCE LISTING

<160> NUMBER OF SEQ ID NOS: 12

<210> SEQ ID NO 1
<211> LENGTH: 32
<212> TYPE: DNA
<213> ORGANISM: artificial sequence
<220> FEATURE:
<223> OTHER INFORMATION: primer

<400> SEQUENCE: 1
cgggatcctg gtgtccgaca gcgactatgt cg                                32

<210> SEQ ID NO 2
<211> LENGTH: 34
<212> TYPE: DNA
<213> ORGANISM: artificial sequence
<220> FEATURE:
<223> OTHER INFORMATION: primer

<400> SEQUENCE: 2
gctctagagg cccatctcct cgagcaggat gcgc                              34

<210> SEQ ID NO 3
<211> LENGTH: 48
<212> TYPE: DNA
<213> ORGANISM: artificial sequence
<220> FEATURE:
<223> OTHER INFORMATION: primer

<400> SEQUENCE: 3
ggcaagggcg gcatcggcaa gctgcaggcg ctcgccgaac tgcaggcc               48

<210> SEQ ID NO 4
<211> LENGTH: 48
<212> TYPE: DNA
<213> ORGANISM: artificial sequence
<220> FEATURE:
<223> OTHER INFORMATION: primer

<400> SEQUENCE: 4
ggcctgcagt tcggcgagcg cctgcagctt gccgatgccg cccttgcc               48

<210> SEQ ID NO 5
<211> LENGTH: 33
<212> TYPE: DNA
<213> ORGANISM: artificial sequence
<220> FEATURE:
<223> OTHER INFORMATION: primer

<400> SEQUENCE: 5
cgggatccga cgcccgagca acacttttcc tcc                               33

<210> SEQ ID NO 6
<211> LENGTH: 34
<212> TYPE: DNA
<213> ORGANISM: artificial sequence
<220> FEATURE:
<223> OTHER INFORMATION: primer

<400> SEQUENCE: 6
gctctagaag ccaaggtcga ggcggtcgaa tacg                              34

<210> SEQ ID NO 7
<211> LENGTH: 48

<212> TYPE: DNA
<213> ORGANISM: artificial sequence
<220> FEATURE:
<223> OTHER INFORMATION: primer

<400> SEQUENCE: 7
ggtaaaggcg gaatcggcaa gctgcaggaa gccgccaagg cggcggcg                        48

<210> SEQ ID NO 8
<211> LENGTH: 48
<212> TYPE: DNA
<213> ORGANISM: artificial sequence
<220> FEATURE:
<223> OTHER INFORMATION: primer

<400> SEQUENCE: 8
cgccgccgcc ttggcggctt cctgcagctt gccgattccg cctttacc                        48

<210> SEQ ID NO 9
<211> LENGTH: 33
<212> TYPE: DNA
<213> ORGANISM: artificial sequence
<220> FEATURE:
<223> OTHER INFORMATION: primer

<400> SEQUENCE: 9
cgggatccgc gagctggaga acgtgatcga gcg                                        33

<210> SEQ ID NO 10
<211> LENGTH: 34
<212> TYPE: DNA
<213> ORGANISM: artificial sequence
<220> FEATURE:
<223> OTHER INFORMATION: primer

<400> SEQUENCE: 10
gctctagatg cccatccggg tgaagtagtc gagc                                       34

<210> SEQ ID NO 11
<211> LENGTH: 48
<212> TYPE: DNA
<213> ORGANISM: artificial sequence
<220> FEATURE:
<223> OTHER INFORMATION: primer

<400> SEQUENCE: 11
ggcaagggtg gcatcggcaa gctgcagatg gtcgtgaagt acggcctg                        48

<210> SEQ ID NO 12
<211> LENGTH: 48
<212> TYPE: DNA
<213> ORGANISM: artificial sequence
<220> FEATURE:
<223> OTHER INFORMATION: primer

<400> SEQUENCE: 12
caggccgtac ttcacgacca tctgcagctt gccgatgcca cccttgcc                        48

US 7,745,023 B2

STRUCTURED MATERIAL FOR THE PRODUCTION OF HYDROGEN

CROSS-REFERENCE TO RELATED APPLICATIONS

This application claims the benefit of U.S. Provisional Application Ser. No. 60/493,745, filed 8 Aug. 2003, which is incorporated herein by reference in its entirety.

STATEMENT OF GOVERNMENT RIGHTS

The present invention was made with government support under Grants No. DE-FG02-01ER63143 and DE-FG02-95ER20184 awarded by the U.S. Department of Energy, and Grant No. DAAD19-01-1-0530 awarded by the U.S. Army Research Office. The United States Government has certain rights in this invention.

BACKGROUND

Metabolically active biological materials (e.g., cells) are phenomenal biochemical catalysts capable of carrying out sequential, stereospecific biochemical reactions. There are significant potential industrial and environmental uses of metabolically active biological materials. They can be used for a variety of purposes such as converting organic waste materials to useful liquid fuels, solvents, gaseous fuels, or to generate electricity in microbial fuel cells. In particular, anaerobes and phototrophic (light trapping) microorganisms that use light to generate cellular energy would be very useful industrial biocatalysts if a method can be found to distribute these living cells uniformly over the surface of electrodes or over a large light-trapping surface area at high cell density.

SUMMARY OF THE INVENTION

The present invention is directed to a composite biological device comprising a layered biostructure comprising at least one biological material embedded in a polymer layer and at least one additional porous layer that does not contain a biological material. Preferably, the biological material can produce $H_2$ gas. Preferably the biological material is not *Thermotoga*. Preferably, the biological material includes one or more species of prokaryotic, eukaryotic, or archean organisms as homogeneous cell populations, mixtures of microorganisms, consortia, mixed-cultures, or unspeciated naturally occurring microbial populations. Biological material may include bacterial cells, algae, plant cells, insect cells, and the like. In some embodiments, examples of bacterial cells include *E. coli, Rhodopseudomonas, Rubrivivax, Rhodobacter, Rhodococcus, Thermotoga, Shewanella, Clostridium*, photosynthetic cyanobacteria, as well as *Geobacter*. For certain embodiments, the bacterial cell is *Clostridium*. For certain embodiments, the bacterial cell is *Rhodopseudomonas*. An example of preferred algae for use within a device of the invention is *Chlamydomonas*. For certain preferred embodiments, the biological material (such as bacteria, yeast, or algal cells) may optionally be recombinant. The biological materials may be aerobic, anaerobic, or any combination thereof. Preferably, the biological material is phototrophic. The biological material may be thermotolerant. Preferably, the biological material is viable, i.e., metabolically active. Preferably, the biological material is genetically optimized for light absorption and/or $H_2$ gas production. Preferably the biological material is embedded within a device.

The present invention significantly expands on the potential industrial and environmental uses of metabolically active (preferably non-growing) biological materials, such as cells, by embedding them within a device (e.g., within a coating or layer of the device). A layer or coating of the device is preferably light transmissible (e.g., transparent or translucent), structured, thin, and porous. A layer or coating may also be non-porous. The device may be multi-layered. A preferred device can be used for a variety of purposes such as generating a gas, such as hydrogen, that can be used as a fuel or for use in fuel cells, for example. Additionally, a device of the invention can be used for degrading environmental pollutants, generating liquid fuels, and degrading organic or inorganic compounds to produce useful chemical intermediates.

More specifically and preferably, a device of the present invention includes a layered biostructure that is thin, porous, highly structured, and multi-layered wherein a polymer layer contains a very high density of embedded biological material. Preferably the biological material is metabolically active but non-growing. Preferably, such a layered biostructure has a very high surface area per unit volume to allow for efficient trapping of light by the embedded biological material. The present invention may also contain electrodes, conductive polymers, and/or inorganic materials such that the metabolic activity (for example, the evolution of hydrogen gas) of the embedded biological materials in contact with the electrodes results in transfer of electrons to produce an electrical current.

Because of its unique thin light transmissible structure, a layer or coating of a device can provide for very efficient biocatalysts for the conversion of organic compounds to useful gases (and preferably electricity) in the presence of light. Prior to this invention, biological materials, such as phototrophic biological materials, were cultivated and suspended in photo bioreactors of significant volume (e.g., lagoons, illuminated stirred tank or static photobioreactors) with limited light-trapping surface area and large liquid volumes that resulted in poor light penetration. None of the previously reported photobioreactors use multiple translucent layers of synthetic polymers in combination with biological materials for the production of $H_2$ gas.

In one embodiment, the present invention provides a device with a light transmissible (e.g., transparent or translucent) biostructure. The light transmissible biostructure includes a structured porous layer that optionally includes at least one metabolically active biological material as an integral component thereof. A portion of the biostructure can include a nonporous latex-derived material. Preferably, the biostructure includes at least one layer of a porous latex-derived material in which biological material, such as living cells, is embedded and at least one layer of a nonporous latex-derived material which forms spacers or channels for fluid to contact the biological material-containing layer. The nonporous material can be used to create a variety of light transmissible structures within the device. For example, nonporous material can define at least one channel or at least a spacer separating layers of cells.

The biostructures of a device of the present invention may be self-supporting or may be disposed on a substrate. The substrate can be reflective material, conductive material, photosensitive, or inert. Preferably, each biostructure is very thin and is comprised of multiple layers, although herein, each biostructure is preferably referred to as a tri-layer biostructure. Each tri-layer includes at least one layer of a polymer (preferably a latex-derived material) and a biological material, a second layer of light transmissible material, and a third layer of spacers or channels formed by a nonpermeable polymer. The third layer may also be constructed from a highly porous material, such as a polymer, that allows fluid to contact the biological material-containing layer. A preferred device of the present invention can include multiples of the tri-layer structure.

An entire multi-layer biostructure is, preferably, no greater than about 500 microns to several millimeters in thickness, more preferably, no greater than about 500 microns in thickness, and most preferably, no greater than about 150 microns in thickness. For certain embodiments, the entire device includes multiple light transmissible layers and is no greater than about 2 millimeters in thickness.

In another embodiment, the present invention provides a device that includes a 3-dimensional porous latex-derived biostructure having at least one metabolically active biological material incorporated therein and the biostructure is disposed on a light reflecting substrate. Preferably, the biological material is phototrophic.

In yet another embodiment, the present invention provides a device that includes a 3-dimensional porous latex-derived biostructure having at least one metabolically active biological material incorporated therein and the porous latex-derived biostructure contains at least two portions of different pore size. Preferably, the biological material is phototrophic.

The present invention also provides a method of making a composite biological device. The method includes depositing at least a first layer comprising a biological material embedded in a polymer onto a second porous layer that does not contain a biological material to form a biostructure having a biological material containing surface. Preferably the biological material produces $H_2$ gas in response to light. An additional third layer of a polymer can optionally be deposited on the biological material containing surface of the device. In some embodiments, the biological material does not include *Thermatoga*. Preferably the biological material is phototrophic. One or more layers may be light transmissible. A transparent material, such as clear polyester sheet, may be used to form a thin translucent biostructure.

In another embodiment, the method includes depositing latex containing a biological material onto a light transmissible material, such as a clear polyester sheet, to form a thin light transmissible biostructure; depositing at least one additional layer of latex on top of the biological material-containing layer to form a nonporous layer of the biostructure in order to direct fluid flow across and through the biological material-containing latex layer. Preferably the biological material is phototrophic. Preferably the biological material produces $H_2$ gas in response to light. The method preferably involves depositing these layers with multi-layer coating or piezoelectric (ink-jet) printing methods. Other known coating and printing methods may be used.

In a preferred embodiment, the present invention provides a device that includes a layer or coating comprising biological material where the biological material includes microbial cells immobilized (preferably, permanently embedded) in one or more layers of a light transmissible polymeric material. Preferably, the cells are genetically engineered to efficiently adsorb light and/or to produce $H_2$ gas. Additionally, they may trap ("fix") atmospheric nitrogen and/or convert it to ammonia when provided with an organic nutrient.

In certain embodiments, the multi-layer translucent biostructure of a device is disposed on a reflective substrate that is capable of deflecting any light not adsorbed by the pigments inside of the biological material, such as phototrophic microbial cells, back into the device for efficient light trapping. In such embodiments, the substrate can also be a photosensitive film or a light-sensitive electronic chip, for example.

In a most preferred embodiment, the present invention provides a device comprising a multi-layer light transmissible biostructure that includes phototrophic biological material where the phototrophic biological material includes microbial cells immobilized (preferably, permanently embedded) in one or more layers of a polymeric material. Preferably, the layers are separated by thin microfluidic channels formed by nonporous latex so that the organic nutrients can be uniformly distributed to the cell-containing layers and useful gases and products resulting from the metabolism of the biological material, such as $H_2$ gas, can be easily removed from the structured coating by fluid flowing through the structured coating.

In certain preferred embodiments, the biostructure includes two to ten tri-layer biostructures. Each tri-layer includes one or more layers of polymer (e.g., latex) plus a biological material, a second layer of transparent material, and a third layer of spacers or channels formed by a light transmissible (e.g., transparent) nonpermeable polymer. The third layer may also be constructed from a highly porous material, such as a polymer. The spacer or channel layer provides a microfluidic flow path for transport of organic compounds to the embedded biological material, such as cells, and transport of useful gases (and optionally electrons, for example) out of the biological material-containing layer. The material of this layer can be conductive and/or can include electrodes.

Also, each tri-layer can include either a conductive polymer or microelectrodes for the transfer of electrons from the surface of the latex-embedded biological material to the conductive substrate thereby generating an electrical current to function as a microbial fuel cell.

In certain embodiments, the biostructure includes two to ten tri-layer biostructures on a reflective substrate that is capable of deflecting light not adsorbed by the biostructures back into them for efficient light trapping. This multi-layer biostructure increases the light trapping surface area by 10-fold or more over the amount of light that would be trapped by a single layer.

The invention also provides *Rhodopseudomonas palustris* mutants that lack a functional molybdenum nitrogenase, a functional iron nitrogenase, a functional vanadium nitrogenase, or any combination thereof. Preferably these *Rhodopseudomonas palustris* mutants are deletion mutants. Examples of these deletion mutants are a ΔvnfH deletion mutant, a ΔanfH deletion mutant, a ΔnifH deletion mutant, a ΔvnfHΔanfH deletion mutant, a ΔnifHΔanfH deletion mutant, and a ΔnifHΔvnfH deletion mutant.

The terms "comprises" and variations thereof do not have a limiting meaning where these terms appear in the description and claims.

As used herein, "a," "an," "the," "at least one," and "one or more" are used interchangeably.

As used herein, "integral" or "integral component" refers to the inclusion of a biological material, such as a metabolically active aerobic or anaerobic microorganism, within a polymer. Such a biological material may be embedded within the polymer such that the polymer restrains the biological material without the need for additional attachment methods. For example, the polymer may surround a portion of the biological material such that it is contained within the polymer. Accordingly, a biological material may be an integral component of a polymer that is included within a device of the invention.

As used herein, "metabolically active" refers to a cell or microorganism that retains the ability to perform coordinated cellular functions. For example, a metabolically active microorganism is able to perform numerous cellular functions that include: gene expression; protein synthesis; adenosine triphosphate production; production of reducing equivalents, such as reduced nicotinamide adenine dinucleotide (NADH), reduced nicotinamide adenine dinucleotide phosphate (NADPH), and reduced flavin adenine dinucleotide ($FADH_2$); deoxyribonucleic acid and ribonucleic acid synthesis and replication; or any combination thereof. A metabolically active microorganism may also be recovered from a device as a viable cell that can produce a colony on an agar plate. Such metabolically active microorganisms can be distinguished from cells that are merely able to catalyze enzymatic reactions but which are not metabolically active.

A "phototrophic biological material" or "phototrophic microorganism" is a biological cell or organism that contains light absorbing pigments and utilizes light to produce metabolic energy, such as the synthesis of adenosine triphosphate.

A "biological material" refers to an intact cell (e.g., whole cell) or an organism.

A "functional nitrogenase" as used herein refers to a nitrogenase enzyme that is able to catalyze the reduction of dinitrogen gas during nitrogen fixation. In comparison, a non-functional nitrogenase is unable to catalyze the reduction of dinitrogen gas.

A "deletion mutant" refers to a microorganism in which a portion of a gene encoding a select nitrogenase has been deleted such that the encoded nitrogenase is no longer able to catalyze nitrogen fixation. A deletion mutant may include mutations in one or more genes that each encodes a nitrogenase. For example, R. palustris encodes an iron nitrogenase, a vanadium nitrogenase, and a molybdenum nitrogenase. Thus, R. palustris deletion mutants include those in which any one, or any combination, or nitrogenases are mutated.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention incorporating different aerobic, anaerobic or phototropic microorganisms, mutants of these microorganisms, or organisms genetically altered to increase their activity, active life, or efficiency to produce certain products of metabolism in these coatings under non-growth conditions. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

FIG. 2 illustrates the genomic organization of the iron nitrogenase (Fe-nitrogenase), the molybdenum nitrogenase (Mo-nitrogenase) and the vanadium nitrogenase (V-nitrogenase) (Larimer et al., Nature Biotechnol., 22:55-61 (2004)).

DETAILED DESCRIPTION OF ILLUSTRATIVE EMBODIMENTS

Figure 1A:
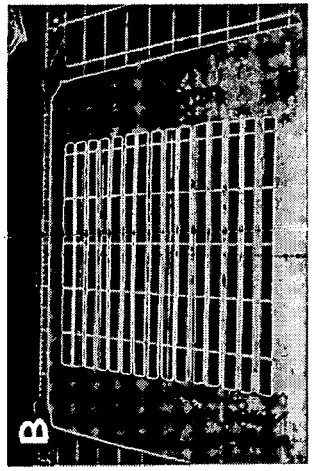
FIG. 1A illustrates an apparatus holding 0.1 millimeter (mm) polyester sheeting.
Figure 1B:
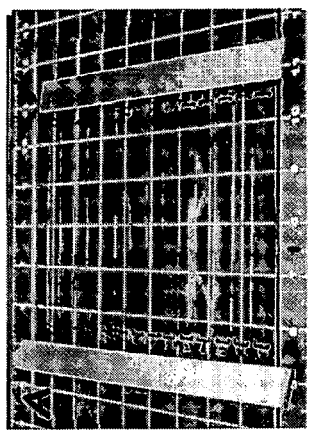
FIG. 1B illustrates a 2-layer pressure sensitive vinyl mask with 15 wells.
Figure 1C:
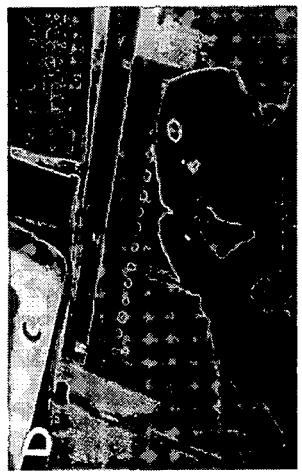
FIG. 1C illustrates the apparatus of FIG. 1A holding 0.1 millimeter polyester sheeting onto which is placed a 2-layer pressure sensitive vinyl mask with 15 wells as shown in FIG. 1B.
Figure 1D:
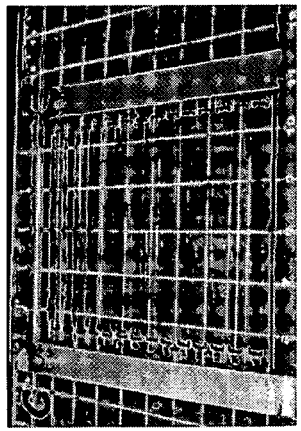
FIG. 1D illustrates delivery of a latex coating mixture into the strip wells as shown in FIG. 1C within an anaerobic glove box having a 90-95% nitrogen and 5-10% hydrogen atmosphere. The latex coating mixture includes 1.2 grams (g) of wet cell paste, 0.3 milliliters (ml) of 0.58 gram/milliliter sucrose, 0.15 milliliter glycerol, 1 milliliter Kathon-free SF091 acrylic/vinyl acetate latex (Rohm and Haas, Philadelphia, Pa.).
Figure 1E:
FIG. 1E illustrates distribution of the latex coating mixture into the strip wells with a small scraper blade.
Figure 1F:
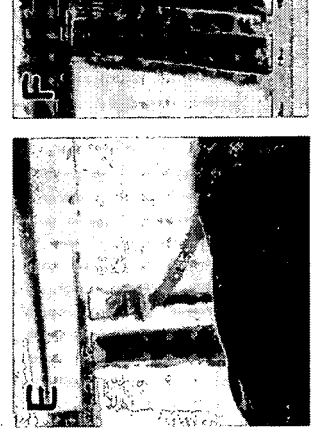
FIG. 1F illustrates drying of the strips under anaerobic conditions at 28° C. and 52% relative humidity for 120 minutes (min) to 150 minutes.
Figure 1G:
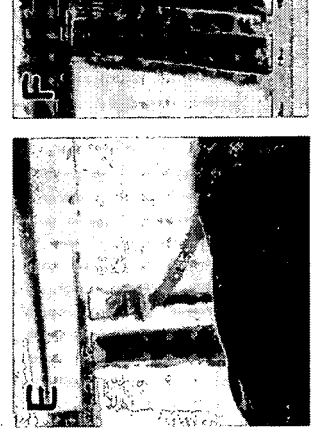
FIG. 1G illustrates removal of the vinyl mask from the R. palustris coatings after drying and cutting of the coatings from the polyester sheet.
Figure 1H:
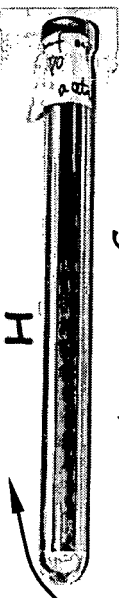
FIG. 1H illustrates a 30 milliliter Balch anaerobe tube containing 10 milliliters of phototrophic medium into which was inserted an R. palustris coating followed by being stoppered, crimped, and incubated with illumination at 30° C.

The present invention provides a device that includes (typically as an integral component thereof) a biological material. Preferably, the biological material is metabolically active. By incorporating metabolically active biological materials, such as cells, as integral components of a multi-layer biostructure, the biostructure can act to stabilize the biological materials, uniformly distribute organic nutrients to the biological materials, and greatly decrease the distance from the biological materials to a solid material (such as an electrode) or to greatly increase the light-trapping surface area to which the biological materials can be exposed. A structured multi-layered device of the present invention expands the potential industrial and environmental uses of metabolically active biological materials.

Preferably, composite biological devices of the present invention may be used for the production of hydrogen gas, which can be used as a fuel. They may also be used for one or more of the following: the production of ammonia fertilizer from atmospheric nitrogen; the production of liquid fuels, such as ethanol, acetone, and butanol, from organic wastes; the production of electricity as a microbial fuel cell using the microbial electron transport chain; the production of electricity as a microbial fuel cell in remote locations; and the production of electricity as a microbial fuel cell in portable (hand-held) electronic devices. A beneficial aspect of this invention for the above applications is that a device can include a layer that contains a biological material, such as cells, in which the biological material is at very high density per unit surface area. Preferably, the device can be stored for long periods of time. In addition, the device may be shipped in a stable form. In some embodiments, a device of the invention can be incorporated into an electronic or industrial device. Preferably, such devices may be activated immediately prior to use.

Preferably, the layers contained within a device are inexpensive because they are comprised of inexpensive polymer lattices and deposited using industrial multi-layer coating techniques. They can be made of both porous and nonporous materials, preferably latex polymers. The latex material can be heat-stable. They include a biostructure, which can include one or more layers of polymeric material. These layers can be continuous or discontinuous and pattern coated, thereby forming patches of light-trapping photo-reactive zones. At least a portion of the biostructure includes a biological material. Preferably, at least a portion of the biostructure includes a nonporous (preferably latex-derived material) used to form microfluidic channels. The biostructure can optionally be disposed on an additional substrate (in addition to the light transmissible material within each tri-layered biostructure) that is porous in certain embodiments.

The biostructure is preferably very thin. Preferably, it is no greater than about several millimeters thick, more preferably, no greater than about 500 microns thick, and most preferably no greater than about 150 microns thick. More preferably, the entire multi-layer biostructure and optional substrate on which the biostructure is disposed is no greater than about 2 millimeters thick.

Preferably, and significantly, the devices of the present invention are stable such that biological materials (e.g., cells or microorganisms) contained within the devices remain metabolically active. Preferably, the biological materials are responsive to light or the presence of organic nutrients after at least about 8 hours under anaerobic ambient conditions when the biostructure is in a hydrated condition. In some examples, biological materials can be removed from a device of the invention and placed into conditions where the biological material will reproduce or grow. More preferably, the devices are stable for at least about 6 months under ambient conditions, and most preferably, indefinitely at a temperature of less than about −10° C., when the biostructure is in a prehydrated (or nonhydrated) condition. For example, a biostructure for use in a device of the invention which contains phototrophic biological material has been shown to remain stable (e.g., maintained at least 75% of its initial phototrophic hydrogen evolution activity when rehydrated) for at least several days after frozen storage at −80° C. in a prehydrated condition. A biostructure of the present invention is also preferably robust such that it can be handled and transported with little or no damage. A device of the invention can be flexible. Preferably, a device of the invention includes an indicator coating that does not delaminate from a supporting substrate, craze, or crack.

A biostructure for use in a device of the invention preferably includes a layer containing immobilized biological material that forms an integral part of the composite device. Typically, such biological material is immobilized in a polymeric layer, which can be in the form of a layer or coating. Preferably, the layer or coating is supported on a substrate (typically, an inert substrate that does not interact or interfere with the function of the device), although a support substrate is not required. A coating that includes at least one biological material may be referred to as a "biological material-containing layer." As used herein, a layer can be continuous or discontinuous. A variety of such layers can be combined to form a variety of structures within the device, such as channels, spacers, etc.

Also, herein a "tri-layer" biostructure may include at least three distinct materials, although multiple layers of each could be used. Preferably, one "tri-layer" biostructure can include at least one layer of a latex-derived material (i.e., the latex polymer that remains after coating of a latex composition), at least one layer of a material that allows fluid to contact the biological material-containing layer, and at least one layer of a transparent or translucent material. The spacer may be highly porous. A plurality of these tri-layer biostructures can be combined to form a device of the present invention.

More specifically, the devices may include a multi-layered construction, which is referred to herein as a biostructure. Preferably, such biostructures include a phototrophic biological material. A polymeric layer that includes the immobilized biological material is typically supported on a light transmissible material (e.g., a transparent or translucent material). This layer can form a porous matrix in which a biological material is embedded (typically, permanently embedded whole living cells or microorganisms) as an integral element of the device. The biological materials can be embedded within a polymeric layer without the polymeric layer adhering to the biological materials. The biological material can be present in the device in multiple layers if desired.

Optionally, and preferably, the biostructure includes at least one interlayer or overlayer (i.e., sealing or sealant layer) of a polymer that does not include biological material. An overlayer on top of the multi-layer biostructure can prevent moisture loss during storage and help prevent the biological material from leaving the first polymeric layer of the biostructure upon rehydration of the biological material with water or a water-based solution. Other layers, which may form channels, spacers, or other structures in a biostructure, are possible as well. Typically, these structures are formed by nonporous material, preferably, nonporous latex-derived polymers.

Thus, as used herein, a biostructure can include one or more biological material-containing polymeric layers and one or more polymeric layers that do not include biological material that can be interspersed between the biological material-containing layers or as overlayers.

In certain embodiments, the biostructures preferably include no greater than about 75% by volume of biological material, and more preferably, no greater than about 50% by volume of biological material. Biological materials that are embedded within a biostructure according to the present invention typically maintain at least about 80% of the original culturability, and preferably have rehydrated culturability that is similar or higher than that of corresponding suspended cells when compared over a period of several weeks.

The light transmissible polymeric layers of the device can be porous or nonporous. Preferably, if they contain biological material, they are porous. Layers that do not include biological material can be porous, less porous, and even nonporous. For certain embodiments, the biostructure includes at least two different porous polymers of different pore sizes.

The porosity of a latex polymeric layer results from the fluid-filled spaces that remain between the polymer particles after polymer particle coalescence. Low porosity or nonporous latex layers are typically formed by latices with very rapid and complete polymer particle coalescence. Examples of these latices include latex paints. Such nonporous polymers can be pattern coated to form nonporous channels, spacers, reservoirs, and wells, for example.

The porosity of latex polymer layers can be controlled by a variety of methods that arrest polymer particle coalescence. Some degree of polymer coalescence or "welding" is typically required for film formation and to embed the biological material. Various methods exist to arrest or control the degree of polymer particle coalescence to obtain optimal porosity. For example, the degree of polymer particle coalescence can be altered by the presence of carbohydrates, or surface active agents, or by polymer particle composition, film formation temperature, and/or drying conditions. Porous latex structures can also be generated using bimodal particle size latex blends or core-shell lattices.

The porosity of a porous layer may also be controlled through use of other methods that are known and that have been described (Gebhard et al., U.S. Pat. No. 6,750,050). In one example, a blend of at least one non-film forming material and at least one film forming polymer is prepared such that the film has a network of pores or channels throughout the film. The non-film forming material may be a polymeric or an inorganic composition. In addition, the non-film forming material may be a hollow polymer particle. Methods to make such hollow polymer particles are known and have been described (Kowalski et al., U.S. Pat. No. 4,427,836).

In another example, a porous core-shell latex polymer is used such that the inner core of the polymer particle is a non-film forming polymer and the shell is a film forming polymer particle. Such a polymer may be prepared through use of a multistage emulsion addition polymerization process in which at least two stages differing in composition are formed in sequential fashion. Such a process usually results in the formation of at least two mutually incompatible polymer compositions, thereby resulting in the formation of at least two phases. Particles produced according to this process are usually composed of two or more phases of various geometries. Examples of these geometries include core/shell or core/sheath particles, core/shell particles with shell phases incompletely encapsulating the core, core/shell particles with a multiplicity of cores, interpenetrating network particles and multi-lobed particles. Such particles are known and have been described (Kowalski et al., U.S. Pat. No. 4,791,151). In some examples, the two-staged emulsion-polymerized addition polymer particles may include from 5% to 35% of a film forming polymer and from 65% to 95% of a non-film forming polymer, based on the total volume of the polymers. Methods to prepare such polymers have been described (Gebhard et al., U.S. Pat. No. 6,750,050).

Large dimension emulsion polymer particles may also be used to prepare a porous layer. Such particles are sometimes referred to as high aspect ratio polymers (HARPS). Methods to make such polymers have been described (Chiou et al., U.S. Pat. No. 5,369,163). The large dimension emulsion polymer particles can be used as non-film forming materials in the preparation of porous layers due to their pore forming ability when used in combination with a film forming polymer. Methods to prepare these types of polymers have been described (Gebhard et al., U.S. Pat. No. 6,750,050).

Latex porosity is commonly measured by monitoring the rate of diffusion of a nonbinding, easily detected, low molecular mass molecule through a latex film using a diffusion apparatus. These indicator molecules rapidly diffuse through (from one side to the other) a highly porous latex film. They diffuse slowly through low porosity films.

Each light transmissible layer, which may be continuous or discontinuous, may contain one or more polymer. Each polymer used is preferably derived from a latex (e.g., water delivered polymer particles), whether it be naturally occurring or synthetic. Other non-latex-derived polymers can also be used if desired. The polymer particles may be monodispersed (all of similar size), polydispersed (broad polymer particle distribution), or specific combinations thereof. The polymers can include, for example, acrylate polymers, vinyl acetate polymers, styrene polymers, butadiene polymers, carboxylate polymers, and blends or copolymers thereof. As used herein a copolymer is a polymer of two or more different types of polymers (including copolymers, terpolymers, tetrapolymers, etc.). The polymers may or may not be cross-linked. Suitable polymers that form translucent layers when dried are commercially available from Rohm and Haas of Philadelphia, Pa., Dupont of Wilmington, Del., H.B. Fuller Co. of Minneapolis, Minn., and GenCorp. of Magadore, Ohio, for example. Preferably, the polymeric material used for embedding biological material includes an acrylic/vinyl acetate or polystyrene copolymer. Preferably, the polymeric material used as an intervening or overlayer includes an acrylic/vinyl acetate copolymer.

The light transmissible polymeric layers (both biological material-containing layer(s) and intervening or overlayer(s) that do not include biological material) can also include additives for various purposes, such as absorbing undesirable material, preventing microbial contamination, and increasing sensitivity. Such additives include, for example, a salt, a pigment, an adsorbent, a liquid crystal, a porosity modifier, a chelating agent, a nutrient, a surfactant, a dye, a photoreactive compound, an antibiotic, an antimicrobial, a bacteriostatic compound, an enzyme, an osmoprotectant, a biopolymer, artificial redox mediators, metal ions, metals, carbonized electrodes, electrocatalytic polymers, or a combination thereof.

Examples of such additives include, but are not limited to: salts such as NaCl, NiCl, $K_2HPO_4$, $KH_2PO_4$, calcium, magnesium, sodium and potassium carbonates; porosity modifiers such as glycerol, glucose, and sucrose; adsorbents such as $CaCO_3$, $CaSO_4$, $MgSO_4$; nutrients such as amino acids (e.g., cysteine) and carbohydrates (such that the material can be frozen or dried and stored for very long periods of time without loss of microbial viability or metabolic activity following coating re-hydration); pigments such as $TiO_2$; dyes such as X-gal (5-bromo-4-chloro-3 indolyl-β-D-galactoside), blue dextran, and Resazurin (7-hydroxy-3H-phenoxazin-3-one-10-oxide); chelating agents such as ethylenediaminetetraacetic acid (EDTA) and ammonium pyrrolidine dithiocarbamate (APDC); surfactants such as FLUORAD FC 430 (3M Co., St. Paul, Minn.); liquid crystals such as p-methoxy benzyliden-p'-n-butoxyaniline (MBBA); enzymes such as peroxidase; photoreactive compounds such as silver halides; bacteriostatic compounds such as NaF; antibiotics such as kanamycin or ampicillin; antimicrobial agents such 1,2-benzisothiazolin-3-one (ICI biocides, Wilmington, Del.); osmoprotectants such as sucrose or trehalose or glycerol; biopolymers such as gelatin; metal ions such as $Mn^{4+}$; metals or carbon used as fuel cell electrodes such as platinum black, platinized carbon cloth; and electrocatalytic polymers such as polyaniline, poly(neutral red), poly(methylene blue). Preferably, the biomaterial-containing layer(s) include glycerol. Preferably, the other polymeric layer(s) include glycerol, bacteriostatic compounds, antibiotics, antimicrobial agents, and/or carbohydrates.

The polymeric layers (both biological material-containing layer(s) and intervening or overlayer(s) that do not include biological material) can also include physical components that can function as electrodes or transmitters. These can include wires, conductive fibers, carbon filaments, carbon cloth, electronic components such as chips, etc. These may or may not be in direct contact with the biological material, although preferably, an electrical conductive material is adjacent to or in direct physical contact with the biological material.

Preferably, the biological material includes one or more species of prokaryotic, eukaryotic, or archean organisms as homogeneous cell populations, mixtures of microorganisms, consortia, mixed-cultures, or unspeciated naturally occurring microbial populations. Biological material may include bacterial cells, algae, plant cells, insect cells, and the like. In some embodiments, examples of bacterial cells include *Rhodopseudomonas, Rubrivivax, Rhodobacter, Rhodococcus, Thermotoga*, photosynthetic cyanobacteria, *Clostridium butyricum*, as well as *Geobacter*. An example of preferred algae for use within a device of the invention is *Chlamydomonas*. For certain preferred embodiments, the biological material (such as bacteria, yeast, or algal cells) may optionally be recombinant. The biological materials may be aerobic, anaerobic, or any combination thereof. Preferably, the biological material is phototrophic. The biological material may be thermotolerant. Preferably, the biological material is viable, i.e., metabolically active. Preferably, the biological material is genetically optimized for light absorption and/or $H_2$ gas production.

The biological material can be in the form cell clumps or cell mats (i.e., a number of different cells living together is some sort of structure), for example. Biological materials may also preferably optimized for desiccation tolerance.

The biological material is preferably genetically engineered to be most efficient in trapping light and/or producing a useful gas such as hydrogen. Other biological materials that could be included can be engineered to produce one or more of the following responses: fix atmospheric nitrogen into ammonia; trap carbon dioxide into storage polymers, such as polyhydroxy alkanoates (PHAs); produce metabolites that are useful liquid fuels or solvents, such as ethanol, acetone and/or butanol; or generate electrons or electrical conductivity.

Methods to optimize $H_2$ production by a biological material are known in the art. For example, strains of *Chlamydomonas reinhardtii* that exhibit improved $H_2$ production in the presence of oxygen have been isolated through use of reported mutagenesis and selection methods (Flynn et al., Int. Jour. Hydrogen Energy, 27:1421-1430 (2002)).

Such a response is typically produced upon illumination with sunlight and irrigation with an organic nutrient. For example, hydrogen production by the action of the intracellular nitrogenase enzymes of *Rhodopseudomonas palustris* entrapped in a latex coating occurs when the coating is submerged in a buffer containing acetate, malate, succinate, or benzoate with a nitrogen-free atmosphere and illuminated. Significantly, many of these responses (such as gas evolution or electrical current) can be measured such that the material being detected can be quantitatively measured. Such responses can be transmitted to a detector, battery, or electronic devise optionally with the aid of a transmitter. The detector and optional transmitter may be part of the device, either forming a part of the biostructure or incorporated into a substrate on which the biostructure is disposed.

A biostructure of the invention can include multiple layers that each include a biological material. The biological material contained within each layer may be the same or different. In some examples, a layer of the biostructure of a device of the invention may include biological material that produces $H_2$ gas while layers above and below the layer may include biological material that does not produce $H_2$ gas. As such, the biostructure of a device of the invention may include numerous types of biological materials.

In addition to the bacteria mentioned above that can produce $H_2$ gas, examples of other suitable bacterial cells include, but are not limited to, *E. coli* and *Shewanella putrifaciens*. For example, *E. coli* and *Shewanella putrifaciens* can be used for the generation of electricity. *Clostridium butyricum* can be used for the generation of hydrogen or electricity. More specific details about incorporation of such bacteria into the present invention are presented in FIGS. 1A-1H.

For particularly preferred embodiments, the biological material incorporated into the materials and devices of the present invention includes the bacterium *Rhodopseudomonas palustris*. This bacterium can produce hydrogen in cells grown with dinitrogen gas as a sole nitrogen source, as compared to ammonia grown cells. *R. palustris* is one of the few species of purple non-sulfur bacteria that can degrade plant lignin monomers and other aromatic compounds (Sasikala and Ramana, Adv. Microb. Physiol., 39:339-377 (1998)). *R. palustris* also has the unique ability to derive electrons from green plant-derived material for $H_2$ production, using only light as the energy source.

Figure 3:
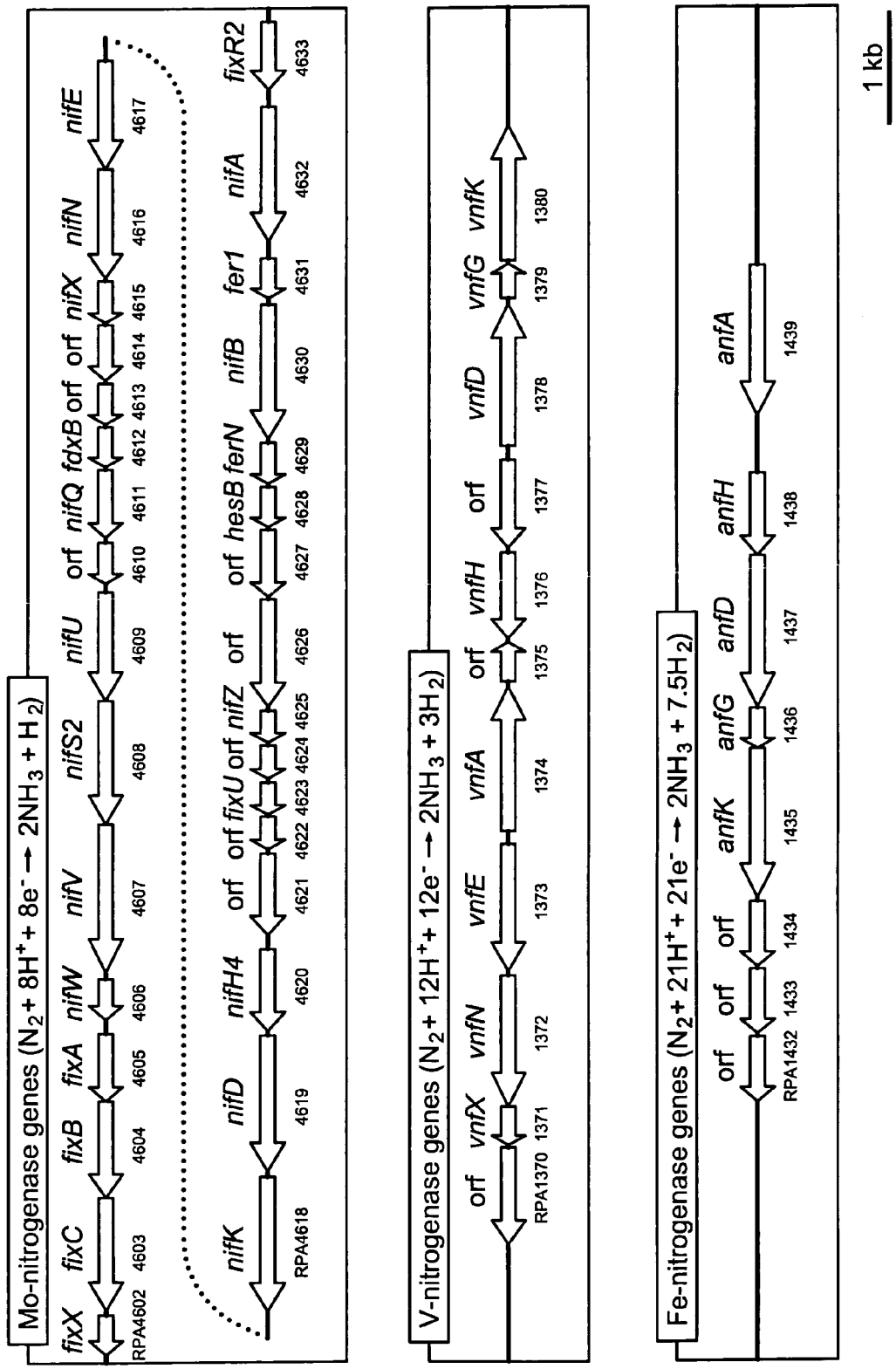
FIG. 3 illustrates the organization of the molybdenum, vanadium and iron nitrogenase gene clusters in R. palustris. The stoichiometrie of $H_2$ production for each nitrogenase is indicated. The arrows indicate the direction of transcription for each gene and the identify of each gene is provided above each arrow. The loci of each gene is indicated by the number below each arrow. A marker bar is provided to indicate the length corresponding to 1 kilobase (kb) of nucleotide sequence. The complete genome sequence of Rhodopseudomonas palustris is reported in Larimer et al., Nature Biotechnology, 22:55-61 (2004) and in Genbank under accession number BX571963. The nucleotide sequence of each gene is also reported in Larimer et al., Nature Biotechnology, 22:55-61 (2004) and in Genbank under accession number BX571963, as well as additional accession numbers for each gene. For example, the amino acid sequence of nifW is reported in Genbank under accession number CAE30046 and the nucleotide sequence is reported in Genbank under accession number NC_005296.

*R. palustris* has nifHDK and associated accessory genes predicted to encode a molybdenum cofactor-containing nitrogenase similar to that found in all nitrogen-fixing bacteria. *R. palustris* also has both vnfGHDK and anfGHDK genes predicted to encode alternative vanadium-cofactor and iron-cofactor containing nitrogenases, respectively. The organization of the three *R. palustris* nitrogenases are illustrated in FIG. 2 and FIG. 3 as well as in Larimer et al., Nature Biotechnology, 22:55-61 (2004).

Mutant strains deleted in various combinations of dinitrogenase reductase (vnfH, nifH and anfH) genes are provided herein. These mutant strains show that *R. palustris* synthesizes three functional nitrogenase isozymes. A ΔnifH ΔvnfH mutant had a phenotype consistent with an iron nitrogenase-only strain. It grows relatively slowly under nitrogen fixing conditions, reduces acetylene to small amounts of ethane and produces six-fold more hydrogen than wild-type cells or a ΔnifH ΔanfH mutant that is predicted to encode only the molybdenum nitrogenase. A ΔnifH ΔanfH strain has the predicted characteristics of a vanadium nitrogenase-only strain. It grows slightly faster than the ΔnifH ΔvnfH strain, also reduces acetylene to a small amount of ethylene and generates about three-fold more hydrogen than wild-type cells. A ΔnifH nifD-miniTn5 strain was also constructed that has the phenotype of a strain that is primarily expressing the vanadium nitrogenase.

Figure 4A:
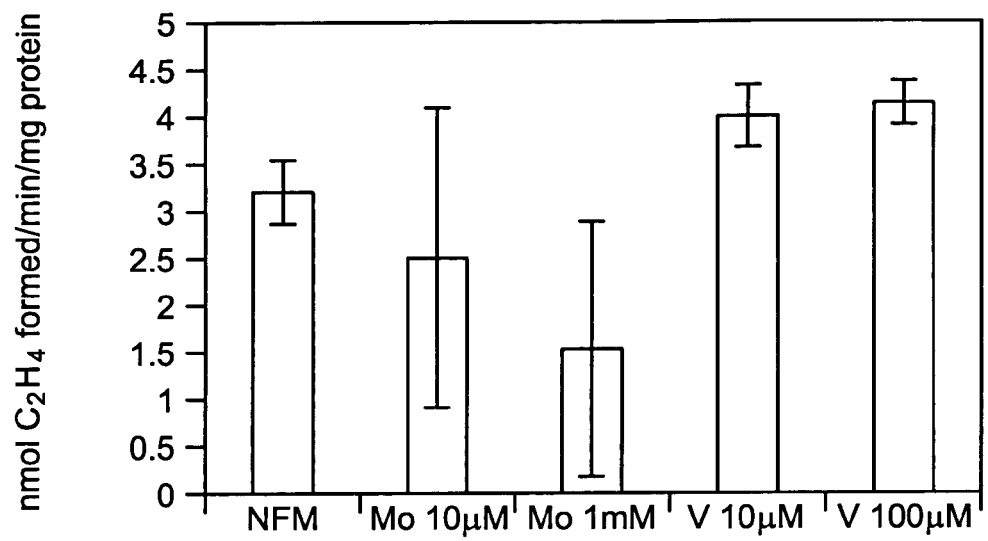
FIG. 4A illustrates the acetylene reduction rate by a ΔnifHΔvnfH strain grown in $N_2$-fixing medium (NFM). The concentration of molybdenum (Mo) and vanadium (V) in the medium is indicated. The $C_2H_6/C_2H_4$ ratio is also indicated. The nanomoles (nmol) of $C_2H_4$ formed/minute/milligram of protein is indicated on the Y-axis.
Figure 4B:
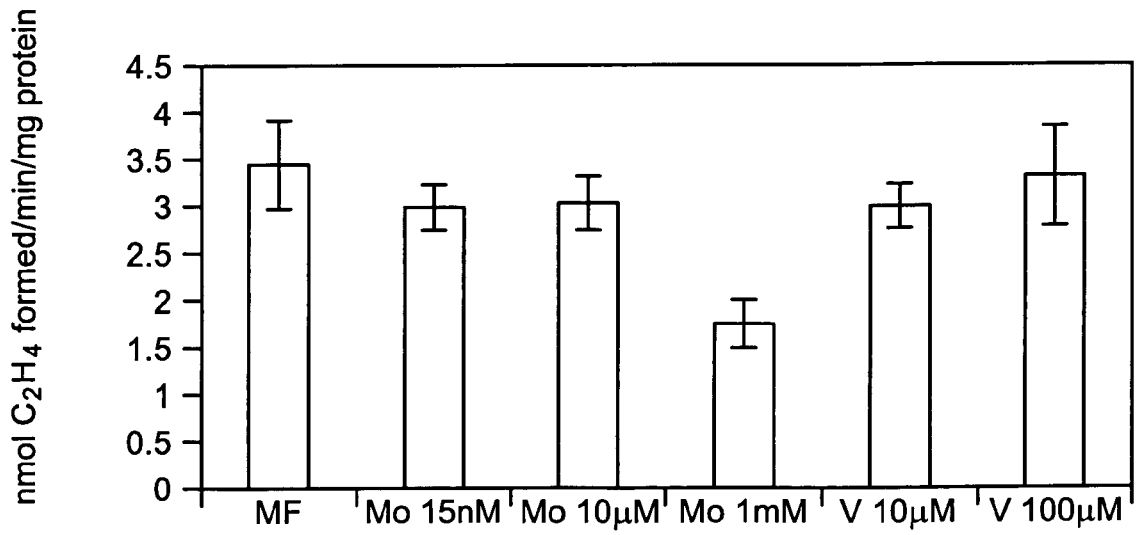
FIG. 4B illustrates the acetylene reduction rate by a ΔnifHΔvnfH strain grown in Mo/V-depleted medium (MF). The concentration of molybdenum (Mo) and vanadium (V) in the medium is indicated. The $C_2H_6/C_2H_4$ ratio is also indicated. The nanomoles of $C_2H_4$ formed/minute/milligram of protein is indicated on the Y-axis.

The two alternative nitrogenases can be expressed in growth media that contains a high concentration of molybdenum, such as 1 mM molybdenum. The iron nitrogenase is active in medium containing substantial levels of vanadium (FIG. 4A and FIG. 4B). A transcriptome analysis reveals that the 30 genes of the nif genes cluster, but not the anf or vnf genes were expressed at, depending on the gene, three-fold to one hundred fifty-fold higher levels, in ammonium grown cells as compared to cells grown with dinitrogen gas as a sole nitrogen source. By contrast, both the ΔnifH ΔvnfH and the ΔnifH ΔanfH strains express all of the *R. palustris* anf, vnf, and nif genes at high levels when grown under nitrogen fixing conditions. It is thought that *R. palustris* differs from other nitrogen-fixing bacteria in that expression of its alternative nitrogenases is not directly regulated by the presence of molybdenum in the growth medium. Instead, *R. palustris* synthesizes the alternative nitrogenases in situations where it is unable to express an active molybdenum nitrogenase regardless of the amount of molybdenum or vanadium that is present. Accordingly, an advantage offered by *R. palustris* is that it can be utilized to generate hydrogen in media that contains metals, such as vanadium, molybdenum and the like. In contrast, the ability to produce $H_2$ by some other types of bacteria is repressed by the presence of metals.

The nitrogenase of *R. palustris* contains three subunits. It is thought that subunits from different types of nitrogenases may combine to form hybrid enzymes. For example, it is thought that subunits belonging to a vanadium nitrogenase and subunits belonging to a molybdenum nitrogenase can combine into a hybrid nitrogenase. Such hybrid enzymes are thought to exhibit improved activity for the generation of $H_2$. These hybrid enzymes are more fully described in the Examples included herein.

*R. palustris* mutants in which hydrogen uptake is reduced or eliminated are provided. Surprisingly, disruption of the uptake hydrogenase in a *R. palustris* mutant has no effect on $H_2$ production. Rather, these mutants exhibit increased hydrogen generation when compared to comparable cells that are able to uptake hydrogen. In some examples, hydrogen uptake can be reduced or eliminated by disruption of the uptake hydrogenase structural genes hupSL. In other examples, hydrogen uptake can be reduced or eliminated by mutation of genes that regulate the uptake of hydrogen, such as hupV and hupU that encode for subunits of the uptake hydrogenase.

Bacterial cells for use in the invention can produce $H_2$ under varying light intensity. For example, bacteria can be used that produce $H_2$ when exposed to very high light intensity, very low light intensity, and intermediate light intensity. Routine methods can be used to select bacterial cells having varying tolerance to light intensity. For example, bacterial cells can be exposed to a mutagen and then selectively grown under the desired light intensity. Methods to mutagenize bacteria are known and include exposure to chemicals, light, radiation, site directed mutagenesis, and the like. The mutagenized cells can then be selected for their ability to produce $H_2$ when grown under the desired intensity of light.

Bacterial cells for use in the invention can be selected for their ability to produce $H_2$ when exposed to different wavelengths of light. Such cells can be mutagenized and then grown under light of a desired wavelength. Cells that produce $H_2$ when grown at the desired wavelength can then be selected.

Preferably, the light transmissible (i.e., light transmissive) biostructure (preferably, in the form of a 3-dimensional biostructure) is supported on a substrate. The substrate can interface with the biostructure if it includes a detector, transmitter, or conductive electrodes. Typically, however, the substrate is an inert light reflective substrate, which is one that does not take part in or interfere in the function of the device. The substrate can be in a wide variety of forms, such as a film, wire, membrane, filament, foam, etc., including combinations of such materials. It can be transparent or translucent. It can be made of a wide variety of materials, which may be porous or nonporous, synthetic or naturally occurring, including metals, glasses, ceramics, carbon, and organic polymers (e.g., nylon, polyester, polycarbonate, and polyacetate). Examples of substrates include paper, woven or nonwoven carbon fiber mats, plastic sheets, etc. The substrate can include electronic components, such as electrodes, and semiconductor devices.

The methods of detection of the flow of electrons include various detection mechanisms. For example, such methods can involve anodes connected to circuits.

The layers of the biostructures and devices of the present invention, with or without biological material incorporated therein, may be formed, for example, by a wide variety of methods, including, for example, draw down coating, slot coating, die coating, spin coating, gravure coating, or piezo-electric or acoustic printing (e.g., inkjet or laser jet printing having piezo-electric or acoustic pumps). Alternatively, gas stream deposition methods can be used.

Typically, the biological material-containing layer(s) are dried prior to the overlayer(s) being applied. A typical coating process of a polymeric layer on a substrate can be carried out at temperatures varying from about 4° C. to about 95° C. under conditions of between 40% and 100% relative humidity. The coating method preferably provides good control over biological material distribution and coating thickness which leads to easily standardized responses or measurements. Alternatively, however, the layers can be simultaneously coated or coated sequentially without intervening drying steps, if so desired. The layers may also be pattern coated.

Pattern coating of rapidly coalescing latex facilitates formation of device biostructures consisting of, for example, nonporous latex walls, dams, channels, spacers, or barriers to restrict gas and liquid flow or diffusion. This pattern coating method can be repeated multiple times to deposit nonporous latex polymer to a predetermined thickness or height. Using this method, device structures such as channels, reservoirs, microwells, etc., can be made. This same method can also be used to generate complex three-dimensional (3-D) interconnected arrays of microfluidic channels, which are regions of the pattern coating containing integral biological material (preferably, substantially permanently entrapped biomaterial).

A particularly preferred method of forming the thin translucent layers of the biostructures of the devices of the present invention is through the use of piezo-electric or acoustic printing (e.g., ink jet or laser jet printing). This method, compared to rod, bar, or slot coating methods can immobilize biomaterial in high resolution multilayer biostructures, which can be in the form of a patch, of such high density (e.g., number layers per unit surface area) and high specific activity (e.g., number of cells per biostructure) that remarkable gains can be realized in light trapping efficiency, phototrophic sensitivity, biocatalyst volumetric activity, and productivity. This technique can eject or jet biological material in pico-liter sized droplets. Polymeric material can be combined with the biological material or applied separately by using two fusing streams. Millions of single droplets can be deposited in ultra-high densities (e.g., greater than about 1000 dots per inch (dpi)) at very high rates.

A suitable printing apparatus may include ink-jet heads containing several rows of nozzles (e.g., 32 nozzles in 4 rows), each nozzle acting as a separate pump and each row feeding from a separate reservoir, which allows mixing of at least 4 different liquid streams as they are deposited resulting in creation of one or multiple gradients during deposition. A multi-channel wash and refill position may be incorporated into the apparatus so that individual rows of nozzles can be washed and refilled any number of times with new media as a part of the printing operation. Current piezo-electric pumps can deposit 6 pL ($6\times10^{-12}$ L) in 45 micron droplets. The corresponding density of individual immobilized cell drops one drop diameter apart is $12.3\times10^3$ drops/cm$^2$ or $7.4\times10^6$ drops on an 8.5×11 inch sheet.

Using such printing techniques, a wide variety of reaction zones can be created, each with its own micro-environment. For example, regions of various antibiotic concentrations can be generated by depositing different amounts of liquid from nozzles connected to separate reservoirs on a print head.

The devices may optionally include a removable film (a "top" film) that protects the biomaterial containing layers. This top or protective film is typically a layer of foil, although it could be a layer of cellulose acetate, poly L-lysine, or a wide variety of other synthetic or natural membrane-like materials. The devices may also optionally include a removable film (a "bottom" or protective film) that protects the supporting substrate, such as a light-sensitive electronic chip.

Figure 5:
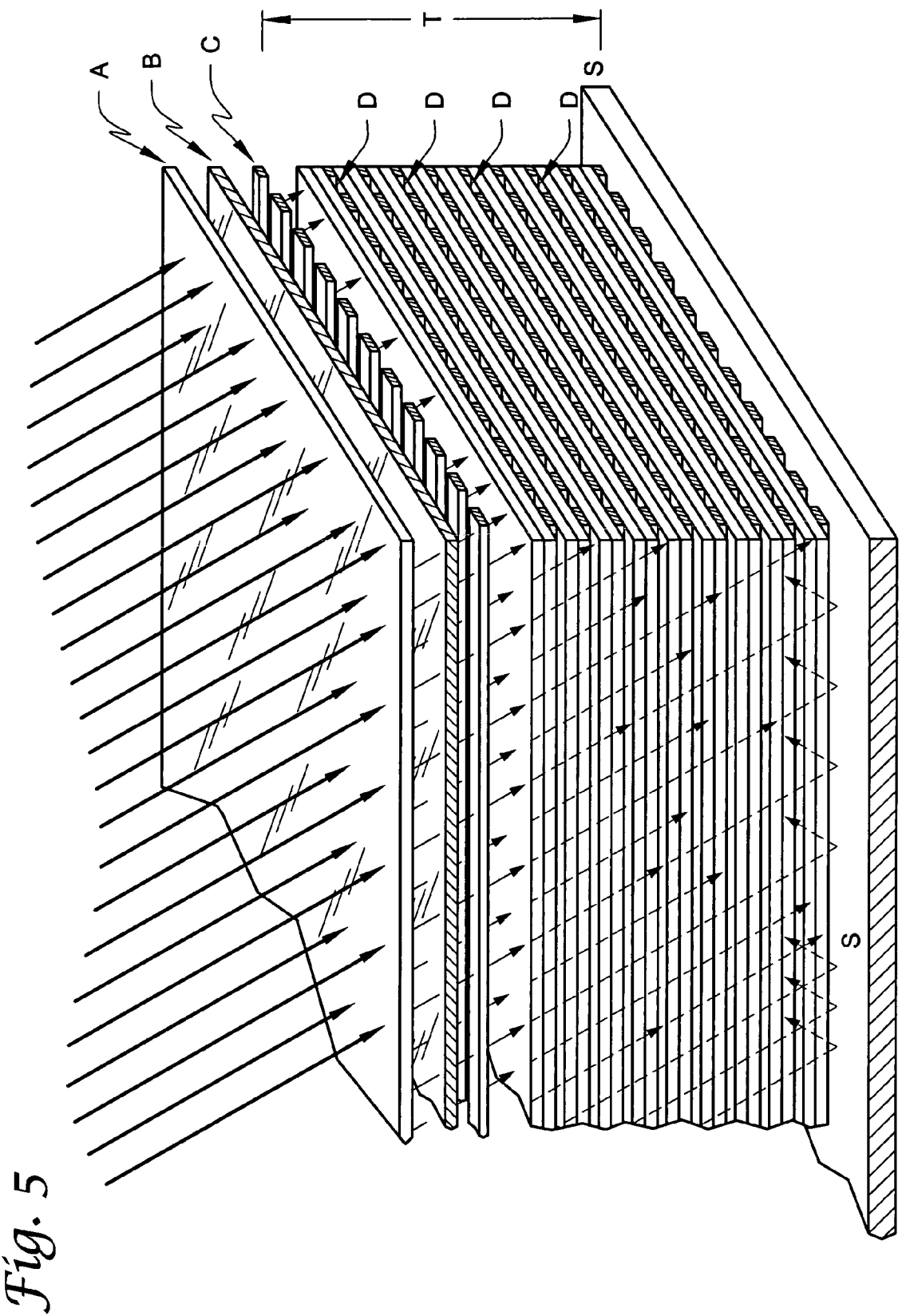
FIG. 5 illustrates a basic structure for a multi-layer device according to the present invention. The device includes a 10-layer biostructure where each layer is formed by a tri-layer coating of: a light transmissible layer of latex plus biological material (A) (specifically, a layer containing 50% (volume/volume) of microorganisms), a light transmissible material (B) (specifically a clear polyester material), and a light transmissible spacer or channel layer (C) creating microfluidic channels. This spacer or channel layer may be highly porous. The entire coating is on a light-reflective substrate (S), which could be a porous substrate. Organic nutrients flow to the biological material through micro-channels channels (D) formed by the channel layer (C). Products of metabolism, such as evolution of hydrogen gas or the production of liquid fuels, flow out of the coating through these same channels (D). The arrows indicate fluid flow of organic nutrients to the cell layers through the microfluidic channels. "T" indicates the total thickness.

FIG. 5 shows a basic, preferred, structure for a multi-layer device according to the present invention. The device includes a 10-layer biostructure where each layer is formed by a tri-layer coating of: a light transmissible (translucent) layer of latex plus biological material (A) (specifically, a layer containing 50% (volume/volume) of microorganisms), a light transmissible (transparent) material (B) (specifically a clear polyester material), and a light transmissible (transparent) spacer or channel layer (C) creating microfluidic channels. The channel layer may be highly porous. The entire coating is on a light-reflective substrate (S), which could be a porous substrate. Organic nutrients flow to the biological material through micro-channels (D) formed by the channel layer (C). Products of metabolism such as evolution of hydrogen gas or the production of liquid fuels flow out of the coating through these same channels (D). The light-trapping surface area of this example is ten times the light trapping area of a single layer. The arrows in FIG. 1 indicate fluid flow of organic nutrients to the cell layers through the microfluidic channels. "T" indicates the total thickness as specified in the illustrative embodiments.

A device of the invention having a multi-layer biostructure can have one type of biological material, such as a microorganism, contained therein. Alternatively, the device can include more than one type of biological material. In one example, a device may contain one to one hundred different types of biological materials. In another example, a device may contain one to fifty different types of biological materials. In another example, a device may contain one to twenty different types of biological materials. In still another example, a device may contain one to ten different types of biological materials. The individual layers of a device having multiple layers can include a single type of biological material or numerous different types of biological materials. For example, each individual layer of a multi-layer biostructure can include a single type of biological material with a different type of biological material included within each individual layer.

A preferred device of the invention having a multi-layer biostructure can be constructed such that biological materials, such as microorganisms, are selected for inclusion within each layer that have light absorption characteristics that are matched to the light conditions present at each layer. For example, biological materials that prefer high intensity light can be placed on the top layer of a multi-layer biostructure where they will be exposed to the highest intensity light. Biological materials that prefer low intensity light can be included within the bottom layer of a multi-layer biostructure where they will be exposed to less intense light. In this manner, biological materials having varying preference for light intensity can be placed on intermediate layers of a multi-layer biostructure to match their preference for light intensity. In addition, biological materials can be included within a layer of a multi-layer biostructure depending on their ability to utilize the wavelength of light present on a given layer. For example, some coatings used to construct the layers of a multi-layer biostructure may block certain wavelengths of light from passing through a given layer. Thus, a biological material that is able to utilize wavelengths of light that are able to pass through one or more layers of a multi-layer biostructure can be positioned in a lower layer to more efficiently utilize the available light on the lower layer.

Additional device configurations and methods that may be utilized to create a device of the invention are exemplified in International Application Number PCT/US99/21581 that was published on 23 Mar. 2000 and has International Publication Number WO 00/16098.

The coatings used to create the individual layers of a device having a multi-layer biostructure can be the same or different. For example, different coatings may be placed at different levels of the multi-layer biostructure to selectively filter light passing through the multi-layer biostructure. In another example, the refractive index of the coating may be matched to a type of phototrophic biological material that is to be placed within a certain layer of a multi-layer biostructure.

Objects and advantages of this invention are further illustrated by the following examples, but the particular materials and amounts thereof recited in these examples, as well as other conditions and details, should not be construed to unduly limit this invention.

EXAMPLES

Example 1

Method for Preparing Coatings of *Rhodopseudomonas palustris*

Bacterial Strains and Media. *Rhodopseudomonas palustris* mutant strains derived from strain CGA009 that express only a single nitrogenase enzyme were constructed by methods of in-frame deletion of genes encoding the two other alternative nitrogenases according to methods similar to those described in Ferrandez et al., J. Bacteriol. 184:4374-4383 (2002). Materials are commercially available from sources such as GIBCO/BRL, Gathersburg, Md., or Promega, Madison, Wis. SacB suicide vectors are in the public. *R. palustris* strains such as CGA009 are in the public. Strain CGA009 is deposited with the American Type Culture Collection under accession number BAA-98. The complete genome sequence of *R. palustris* CGA009 has Genbank/EMBL/DDBJ accession number BX571963. The strain is more fully described in Larimer et al., Nature Biotechnology, 22:55-61 (2004). *R. palustris* is grown in various mineral media including photosynthetic medium (PM) described in Kim and Harwood, FEMS Microbiol. Lett., 83:199-204 (1991).

Growth conditions. Cells were grown for preparation of latex strips in 200 ml serum bottles containing 50 ml of photosynthetic medium with 22 mM sodium acetate and no source of fixed nitrogen at 30° C. with incandescent illumination. The bottle headspace contained 90% nitrogen+10% hydrogen.

Coating Materials. Harvested *Rhodopseudomonas palustris* cells were mixed with glycerol, sucrose, and acrylic/vinyl acetate copolymer latex (Rohm and Haas, Philadelphia, Pa.) in a ratio depending on the number of cells immobilized. Commonly used was 1.2 grams of cell paste, 0.3 ml 50% (w/w) glycerol, 0.3 ml of a sterile 0.58 g/ml sucrose solution, and 1 ml latex, which were mixed together. The cell-polymer mixture was coated in an anaerobic glove box (90% nitrogen, 10% hydrogen atmosphere) into 1 cm by 12.5 cm wells formed using a pressure sensitive vinyl mask onto a transparent polyester template using a small spatula (or Mayer bar) at room temperature, as illustrated in greater detail in FIG. 1A-1H. After the coated layer was dried at 50% relative humidity for 120 to 150 minutes in the anaerobic glove box, the vinyl template was removed, and the polyester strips inserted into anaerobe tubes, filled with 10 ml of buffer containing an organic nutrient such as acetate, capped, and removed from the anaerobic glove box, the gas phase flushed with purified argon for 60 minutes to remove nitrogen gas, and illuminated at 30° C.

Latex Materials. Rovace SF091 latex without Kathon biocide but containing 0.4 volume sucrose per volume dry latex polymer and sufficient glycerol to sustain cell viability was used. Cell coat material: 1.2 g of wet cell pellet (centrifuged in an anaerobic atmosphere) gently resuspended in 0.3 ml 50% (v/v) glycerol in water with 0.3 ml sterile sucrose solution (0.58 g/ml) and 1 ml Rovace SF091 added immediately prior to coating.

Template, Mask, Spacer and Coating Materials. Coatings were cast on clear 4 mil polyester (DuPont Melinex 454, Tekra Corp., NJ). Templates and masks were made from two layers of pressure sensitive clear vinyl (42.6 microns) (μm) (Con-Tact, Stamford, Conn.).

Preparing Template Masks. A template mask is a sheet of pressure sensitive vinyl mask with 15—1 cm by 12.5 cm sections cut out where the coating liquid is to contact the underlying clear polyester substrate. A vinyl template can be applied on top of a clean transparent polyester material that has already been cut into strips to fit into the anaerobe tubes. The polyester substrate is taped to a glass plate. After application of one or more layers of latex plus cell mixture into each well using a pipette, distributing the latex plus cell layer with a small spatula, followed by drying in the anaerobic glove box at >50% relative humidity, the vinyl mask can be removed to expose the 1 cm by 12.5 cm strip layer beneath. Each template mask was generated by manually cutting with a razor blade. Templates with nicks or tears were discarded since these would prevent them from separating from the substrate without tearing. Templates were applied onto the substrate or coating by rolling it onto it with a hard rubber roller (Orcon Corporation, Union City, Calif.). Portions of the mask covered the perforations in the polyester substrate, thereby creating strip-like channels between the polyester substrate perforations. This method created 15 uniform 1 cm by 12.5 cm strips or channels with a depth of approximately 85 μm (microns). This process is illustrated in FIG. 1A-1H.

Coating of Latex Polymers. All coating layers were coated using either a small spatula for individual wells or the entire sheet mask of 15 wells could be coated all at once using wire wound rods (Mayer bars) with a wire diameter of 0.7 mm (R. D. Specialities, Webster, N.Y.).

Testing of Individual Layers in Micro Photo Bioreactors. Individual 1 cm by 12.5 cm latex coatings of *Rhodopseudomonas palustris* on clear 0.1 mm thick polyester strips were tested for hydrogen production in an argon atmosphere in 30 ml Balch anaerobe tubes at 30° C. illuminated with a 60 watt incandescent light bulb.

Detection of Hydrogen Evolution. Hydrogen evolution from the coatings was detected by periodically removing a volume of gas from the anaerobe tube using a syringe and injecting this gas sample into a gas chromatograph equipped with a 13× molecular sieve column and a thermal conductivity detector. The quantity of evolved hydrogen gas present in the argon atmosphere was calibrated against known gas mixtures of hydrogen by the area under the peak corresponding to the retention time of hydrogen of the detector. Only hydrogen gas was detected.

Figure 6:
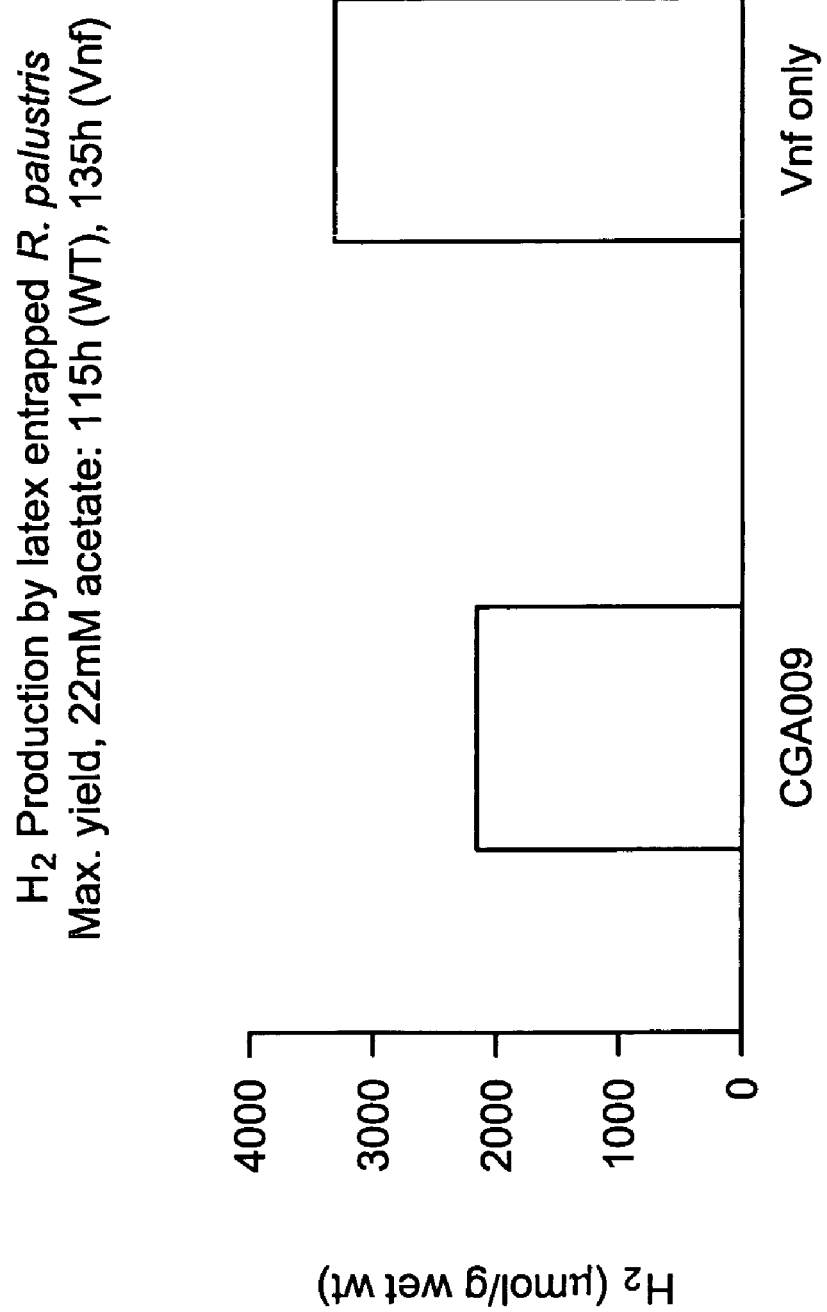
FIG. 6 illustrates $H_2$ production by latex entrapped *R. palustris*. $H_2$ production in micromoles (μmol)/gram wet cell weight is indicated on the Y-axis.

Latex coating micro photo bioreactors. $1.25 \times 10^{-3}$ m² latex biocatalytic coatings of R. palustris were generated from 40 ml of liquid culture. Each coating contained 0.12 grams to 0.22 grams of wet cell paste. Hydrogen evolution from latex coatings is reported as μmol $H_2$/gram wet cell weight/m²/hour. Latex strips of CGA009 frozen in 25% glycerol at −80° C., thawed, and incubated with photosynthetic media acetate medium in the micro photo bioreactors generated hydrogen at a rate of 20 μmol/gram/hour; 15,800 μmol/gram/m²/hour. $H_2$ production by latex entrapped R. palustris is reported in Table 1 and in FIG. 6.

TABLE 1

$H_2$ production by latex entrapped R. palustris with an argon atmosphere

| Strain | Functional nitrogenase | $H_2$ production (rate)* | $H_2$ production (rate)* |
|---|---|---|---|
| Wild-type | molybdenum nitrogenase | 24.7 +/− 8 | 19,760 +/− 6,200 |
| ΔnifHΔanfH | vanadium nitrogenase | 33.7 +/− 8 | 26,460 +/− 6,900 |
| ΔnifHΔvnfH | iron nitrogenase | 5 +/− 1 | 4,000 +/− 510 |

*μmol/gram wet cell weight/m²/hour

Example 2

Characterization of $H_2$ Production by R. palustris

Growth conditions. R. palustris cells were grown in 30 ml anaerobic tubes containing 10 milliliters of photosynthetic media with 22 mM sodium acetate and no source of fixed nitrogen at 30° C. in the presence of incandescent illumination. The headspace (20 ml) contained 90% nitrogen+10% hydrogen.

Hydrogen measurements. Samples were obtained using a syringe from the tube headspace. Hydrogen was detected using a 5890 series II gas chromatograph containing a molecular sieve 13× column and thermal conductivity detector. Nitrogen was used as the carrier gas. Hydrogen evolution from cultures is expressed as μmol $H_2$/milligram total cell protein.

Figure 7:
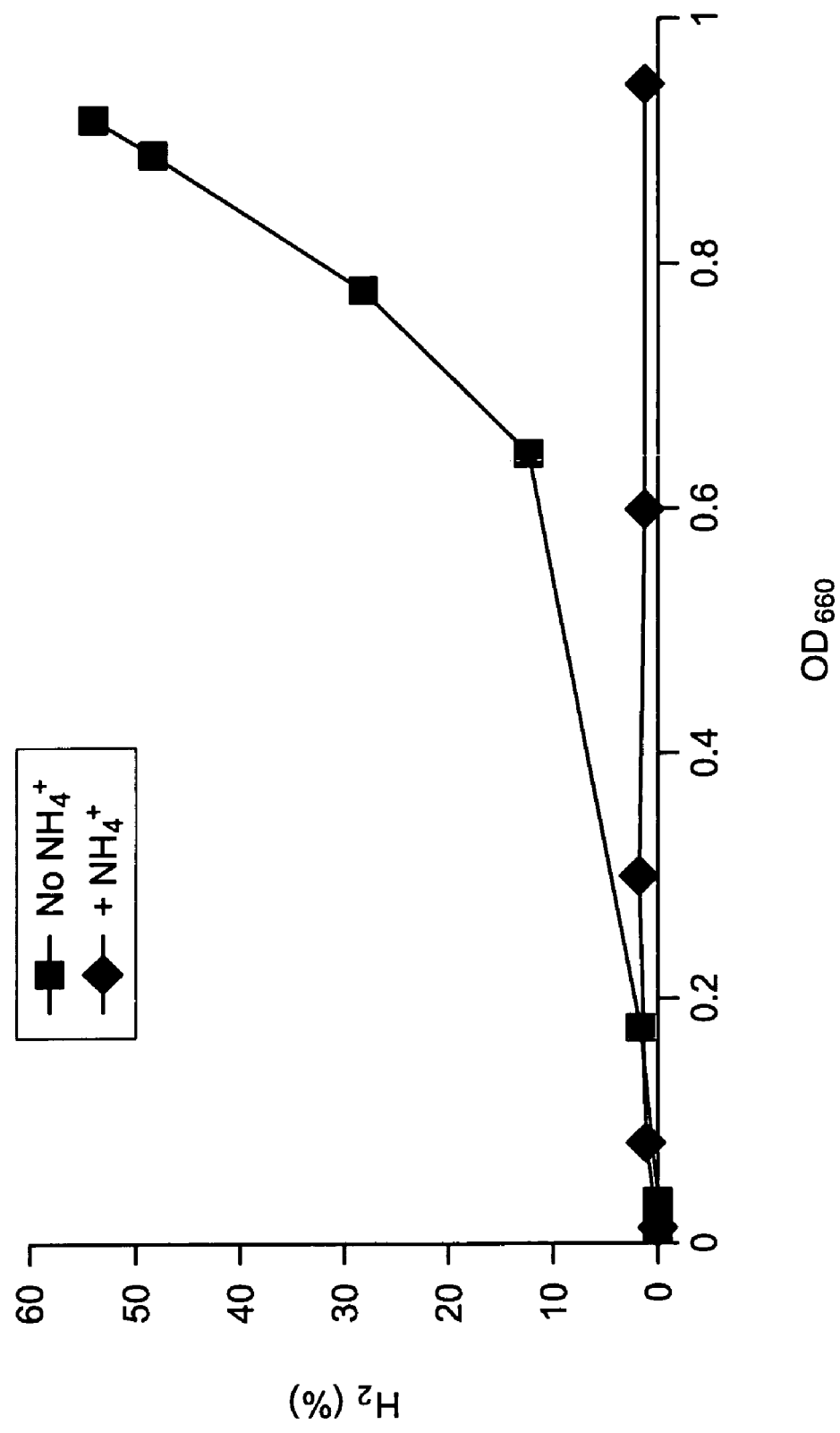
FIG. 7 illustrates that growing *R. palustris* cells generate hydrogen under nitrogen fixing conditions. $H_2$ production is indicated on the Y-axis. The optical density of the cell culture at 600 nanometers (nm) is indicated on the X-axis. The line containing diamonds indicates $H_2$ production in the presence of $NH_4$. The line containing squares indicates $H_2$ production in the absence of $NH_4$.

Hydrogen production by R. palustris cells. Hydrogen production by R. palustris cells grown under nitrogen fixing conditions is illustrated in FIG. 7. Hydrogen production by R. palustris cells in the presence of different carbon sources is reported in Table 2 and hydrogen production by R. palustris mutants using different nitrogenases is reported in Table 3. The stoichiometrie of $H_2$ production by different R. palustris nitrogenases is provided in Table 4.

TABLE 2

Hydrogen production in the presence of different carbon sources

| Carbon Source* | Growing Cells (μmol $H_2$/mg protein) | Final Yield (μmol $H_2$/mg protein) |
|---|---|---|
| Malate (10 mM) | 27 | 120 |
| Succinate (10 mM) | 32 | 180 |
| Acetate (18 mM) | 86 | 220 |
| Benzoate (4.5 mM) | 112 | 230 |
| Cyclohexanecarboxylate (4.5 mM) | 115 | 327 |

*The more reduced the carbon source supplied, the more $H_2$ is evolved

TABLE 3

Hydrogen production by growing R. palustris cells having different nitrogenase mutations

| Strain | Functional nitrogenase | $H_2$ production (μmol/mg protein) |
|---|---|---|
| Wild-type | molybdenum nitrogenase | 58 +/− 2 |
| ΔvnfHΔanfH | molybdenum nitrogenase | 50 +/− 6 |
| ΔnifHΔanfH | vanadium nitrogenase | 160 +/− 15 |
| ΔnifHΔvnfH | iron nitrogenase | 286 +/− 61 |

TABLE 4

Stoichiometrie of $H_2$ production by different nitrogenases of R. palustris.

| Molybdenum nitrogenase | $N_2 + 8 H^+ + 8 e^- \rightarrow 2 NH_3 + H_2$ |
| Vanadium nitrogenase | $N_2 + 12 H^+ + 12 e^- \rightarrow 2 NH_3 + 3 H_2$ |
| Iron nitrogenase | $N_2 + 21 H^+ + 21 e^- \rightarrow 2 NH_3 + 7.5 H_2$ |

Example 3

Construction and Characterization of R. palustris Mutants

Construction of R. palustris Deletion Mutant Strains. An in-frame deletion of nifH was created by overlap extension PCR as described previously (Ho et al., Gene, 77:51-59 (1989); Horton et al., Gene, 77:61-68 (1989)) with the following modifications. A region of R. palustris CGA009 chromosomal DNA containing approximately 1 kilobase (kb) upstream and 1 kb downstream regions including nifH gene was polymerase chain reaction (PCR) amplified using primers UnifH-BamHI and DnifH-XbaI. The PCR product was gel-purified and using this as a template, two regions were PCR amplified. The primers for the first region were UnifH-BamHI and nifH-delR and for the second region DnifH-XbaI and nifH-delF. A mixture of these two DNA fragments was used (approximately 100 ng) as a template for the third PCR using UnifH-BamHI and DnifH-XbaI primers. The product of the third amplification contained a 792 basepair (bp) in-frame deletion in nifH gene including approximately 0.9 kb upstream and downstream regions, with engineered BamHI and XbaI sites on its 5' and 3' ends, respectively. This product was digested with BamHI and XbaI and was ligated into BamHI/XbaI digested pUC19 yielding pUC-ΔnifH. This plasmid was sequenced to confirm the desired deletion. Then the ΔnifH DNA piece was excised with BamHI/XbaI from pUC-ΔnifH and cloned into pJQ200KS yielding plasmid pJQ-ΔnifH. Similar PCR and cloning strategies and methods were used to construct plasmids pJQ-ΔvnfH and pJQ-ΔanfH containing in-frame deleted vnfH and anfH genes, respectively.

Plasmid pJQ-ΔnifH was then mobilized from E. coli S17-1 into R. palustris CGA009 by conjugation. A single recombination event was selected by growth on a photosynthetic medium (PM) plate containing gentamicin (Gm) (100 μg/ml) (Harwood and Gibson, Appl. Environ. Microbiol., 54:712-717 (1988) and Kim and Harwood, FEMS Microbiol. Lett., 83:199-204 (1991)). A $Gm^R$ but $sucrose^S$ colony was grown in PM with succinate and plated on Sucrose (10%). The $sucrose^R$ colonies were picked and patched on Gm and Sucrose plates. The $Sucrose^R$ $Gm^S$ colonies were screened by colony PCR followed by sequencing for non-polar in-frame nifH deletion mutant (CGA750). Similar recombination strategies and methods were used to construct non-polar vnfH and anfH in-frame deletion mutants (CGA751 and CGA752, respectively) in R. palustris CGA009.

The plasmid pJQ-ΔanfH (containing a 753-bp in-frame deletion in anfH gene) was mobilized into CGA751 strain and a ΔvnfHΔanfH double in-frame deletion mutant (CGA753; $Nif^+$ strain) was screened. Similarly pJQ-ΔanfH was mobilized into CGA750 strain to create ΔnifHΔanfH double mutant (CGA754, $Vnf^+$ strain). Plasmid pJQ-ΔvnfH (containing a 816-bp in-frame deletion in vnfH gene) was mobilized into CGA750 strain to create ΔnifHΔvnfH double mutant strain (CGA755, $Anf^+$ strain). Similarly, the triple mutant, ΔnifHΔvnfHΔanfH (CGA756) was also created by mobilizing pJQ-ΔanfH into CGA755. A ΔnifH nifD-miniTn5 strain was also constructed.

Additional strains, plasmids and primers used to create R. palustris mutants are provided in Tables 5 and 6 below.

TABLE 5

Strains and plasmids

| Strains or Plasmid | Relevant characteristics |
|---|---|
| R. palustris strains | |
| CGA009 | Wild-type; spontaneous $Cm^R$ derivative of CGA001 (Kim and Harwood, FEMS Microbiol. Lett., 83: 199–204 (1991)) |
| CGA750 | ΔnifH derivative of CGA009; 792 bp deleted from gene |
| CGA751 | ΔvnfH derivative of CGA009; 816 bp deleted from gene |
| CGA752 | ΔanfH derivative of CGA009; 753 bp deleted from gene |
| CGA753 | ΔvnfH ΔanfH derivative of CGA009; 816 and 753 bp deleted from vnfH and anfH, respectively |
| CGA754 | ΔnifH ΔanfH derivative of CGA009; 792 and 753 bp deleted from nifH and anfH, respectively |
| CGA755 | ΔnifH ΔvnfH derivative of CGA009; 792 and 816 bp deleted from nifH and vnfH, respectively |
| CGA756 | ΔnifH ΔvnfH ΔanfH derivative of CGA009; 792, 816 and 753 bp deleted from nifH, vnfH and anfH, respectively |
| CGA762 | ΔnifH nifD::Km |
| E. coli strains | |
| DH5α | $F^- \lambda^-$ recA1 Δ(lacZYA-argF)U169 hsdR17 thi-1 gyrA96 supE44 endA1 relA1 φ80lacZΔM15 (Gibco-BRL, Gaithersburg MD) |
| S17-1 | thi pro hdsR hdsM⁺ recA; chromosomal insertion of RP4-2 (Tc::Mu Km::Tn7) (Simon et al., Bio/Technology, 1: 784–789 (1983)) |
| Plasmids | |
| pJQ200KS | $Gm^R$, Mobilizable suicide vector, sacB (Quandt and Hynes, Gene, 127: 15–21 (1993)) |
| pUC19 | $Ap^R$; high-copy-number cloning vector (Yanisch-Perron et al., Gene, 33: 103–119 (1985)) |
| pHRP309 | $Gm^R$, IncQ, lacZ transcriptional fusion vector (Parales and Harwood, Gene, 133: 23–30 (1993)) |
| pHRP311 | $Gm^R$, $Sm^R$, $Sp^R$; negative control plasmid (cassette from cohort vector inserted into pHRP309) (Parales and Harwood, Gene, 133: 23–30 (1993)) |
| pHRP316 | $Ap^R$, $Sm^R$, $Sp^R$; cohort cloning vector for use with pHRP309 (Parales and Harwood, Gene, 133: 23–30 (1993)) |
| pUC-ΔnifH | $Ap^R$, in-frame deletion of nifH constructed by PCR and cloned into BamHI/XbaI sites of pUC19 |
| pUC-ΔvnfH | $Ap^R$, in-frame deletion of vnfH constructed by PCR and cloned into BamHI/XbaI sites of pUC19 |
| pUC-ΔanfH | $Ap^R$, in-frame deletion of anfH constructed by PCR and cloned into BamHL/XbaI sites of pUC19 |
| pJQ-ΔnifH | $Gm^R$, BamHI/XbaI fragment of pUC-ΔnifH cloned into pJQ200KS |
| pJQ-ΔvnfH | $Gm^R$, BamHI/XbaI fragment of pUC-ΔvnfH cloned into pJQ200KS |
| pJQ-ΔanfH | $Gm^R$, BamHI/XbaI fragment of pUC-ΔanfH cloned into pJQ200KS |

TABLE 6

Primers used for the creation of in-frame deletion mutants

Primer designation  Oligonucleotide sequence and description

UnifH-BamHI  5'-CGGGATCCTGGTGTCCGACAGCGACTATGTCG-3'
(SEQ ID NO: 1) (nifH upstream primer)

DnifH-XbaI  5'-GCTCTAGAGGCCCATCTCCTCGAGCAGGATGCGC-3'
(SEQ ID NO: 2) (nifH downstream primer)

nifH-delF  5'-GGCAAGGGCGGCATCGGCAAGCTGCAGGCGCTC
GCCGAACTGCAGGCC-3'
(SEQ ID NO: 3) (nifH in-frame deletion forward primer)

nifH-delR  5'-GGCCTGCAGTTCGGCGAGCGCCTGCAGCTTGCCG
ATGCCGCCCTTGCC-3'
(SEQ ID NO: 4) (nifH in-frame deletion reverse primer)

UvnfH-BamHI  5'-CGGGATCCGACGCCCGAGCAACACTTTTCCTCC-3'
(SEQ ID NO: 5) (vnfH upstream primer)

DvnfH-XbaI  5'-GCTCTAGAAGCCAAGGTCGAGGCGGTCGAATACG-3'
(SEQ ID NO: 6) (vnfH downstream primer)

vnfH-delF  5'-GGTAAAGGCGGAATCGGCAAGCTGCAGGAAGCC
GCCAAGGCGGCGGCG-3'
(SEQ ID NO: 7) (vnfH in-frame deletion forward primer)

vnfH-delR  5'-CGCCGCCGCCTTGGCGGCTTCCTGCAGCTTGCCG
ATTCCGCCTTTACC-3'
(SEQ ID NO: 8) (vnfH in-frame deletion reverse primer)

UanfH-BamHI  5'-CGGGATCCGCGAGCTGGAGAACGTGATCGAGCG-3'
(SEQ ID NO: 9) (anfH upstream primer)

DanfH-XbaI  5'-GCTCTAGATGCCCATCCGGGTGAAGTAGTCGAGC-3'
(SEQ ID NO: 10) (anfH downstream primer)

anfH-delF  5'-GGCAAGGGTGGCATCGGCAAGCTGCAGATGGTCG
TGAAGTACGGCCTG-3'
(SEQ ID NO: 11) (anfH in-frame deletion forward primer)

anfH-delR  5'-CAGGCCGTACTTCACGACCATCTGCAGCTTGCCGA
TGCCACCCTTGCC-3'
(SEQ ID NO: 12) (anfH in-frame deletion reverse primer)

Figure 8A:
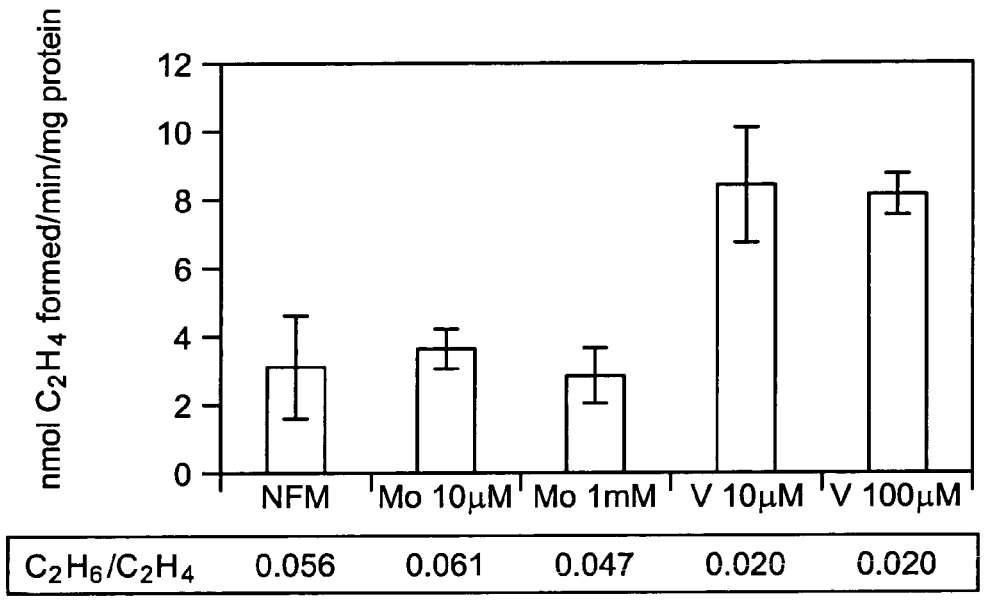
FIG. 8A illustrates the acetylene reduction rate by a nifD:: Km ΔnifH *R. palustris* strain grown in $N_2$-fixing medium (NFM). The concentration of molybdenum (Mo) and vanadium (V) in the medium is indicated. The $C_2H_6/C_2H_4$ ratio is also indicated. The nmol of $C_2H_4$ formed/minute/milligram of protein is indicated on the Y-axis.
Figure 8B:
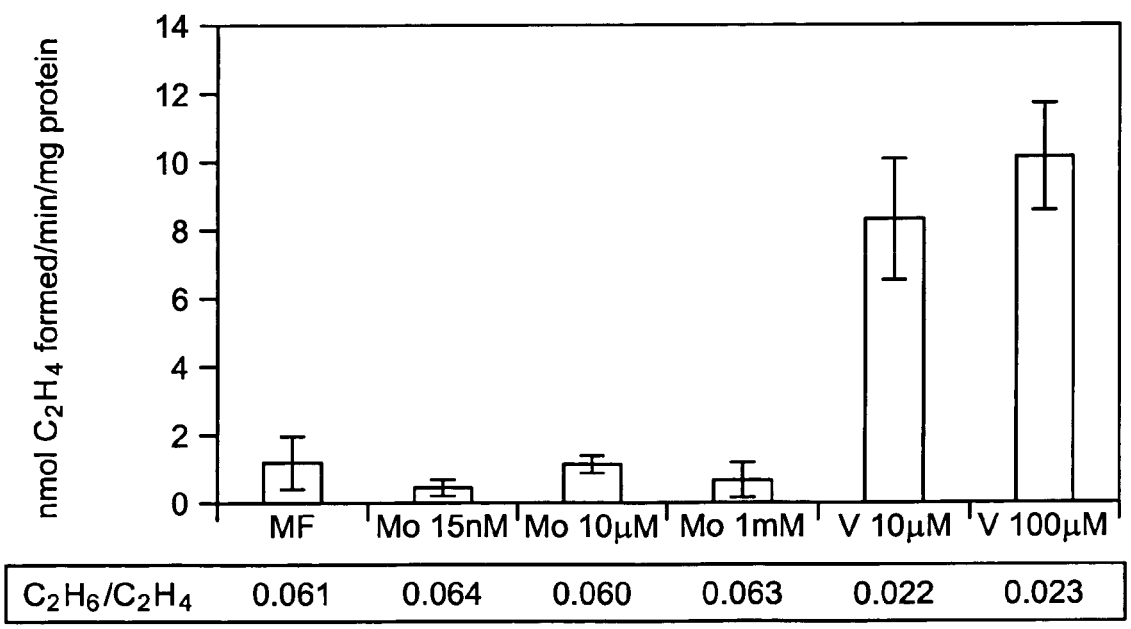
FIG. 8B illustrates the acetylene reduction rate by a nifD:: Km ΔnifH *R. palustris* strain grown in MoN-depleted medium (MF). The concentration of molybdenum (Mo) and vanadium (V) in the medium is indicated. The $C_2H_6/C_2H_4$ ratio is also indicated. The nmol of $C_2H_4$ formed/minute/milligram of protein is indicated on the Y-axis.

Characterization of the R. palustris mutants. The ΔnifH-nifD:Tn5 strain expresses a vanadium nitrogenase activity when vanadium and molybdenum are present, an iron nitrogenase activity when only molybdenum is present, and is thought to be completely defective in the synthesis of the molybdenum nitrogenase. As with the iron nitrogenase-only strain, addition of molybdenum to the nitrogen-fixing growth medium did not repress rates of acetylene reduction by the ΔnifHnifD:Tn5 strain and the amount of ethane produced from acetylene was unaltered. The relative amount of ethane produced by this strain in the presence of molybdenum was indicative of an iron nitrogenase. Vanadium was not included as a trace element in the nitrogen—fixing growth medium initially. Inductively coupled plasma mass spectroscopy analysis indicated that the medium contained less than 2 nM vanadium, and subsequently it was determined that the Δnif-HnifD:Tn5 strain had increased rates of acetylene reduction when grown in medium supplemented with vanadium and that it also produced the relatively small amounts of ethane indicative of an active vanadium nitrogenase (FIG. 8A). Consistent with this, it was determined that the ΔnifHnifD:Tn5 strain behaved as iron-nitrogenase only expressing strains in 8-hydroxyquinoline treated, molybdenum depleted medium, and that addition of molybdenum to the medium did not repress rates of acetylene reduction. Addition of vanadium to the 8-hydroxyquinoline treated medium stimulated rates of acetylene reduction and ΔnifHnifD:Tn5 cells produced ethane in amounts indicative of an active vanadium nitrogenase (FIG. 8B). The nifD::Km ΔnifH strain expresses a vanadium nitrogenase activity when vanadium and molybdenum are present, but an iron nitrogenase activity when only molybdenum is present.

Figure 9A:
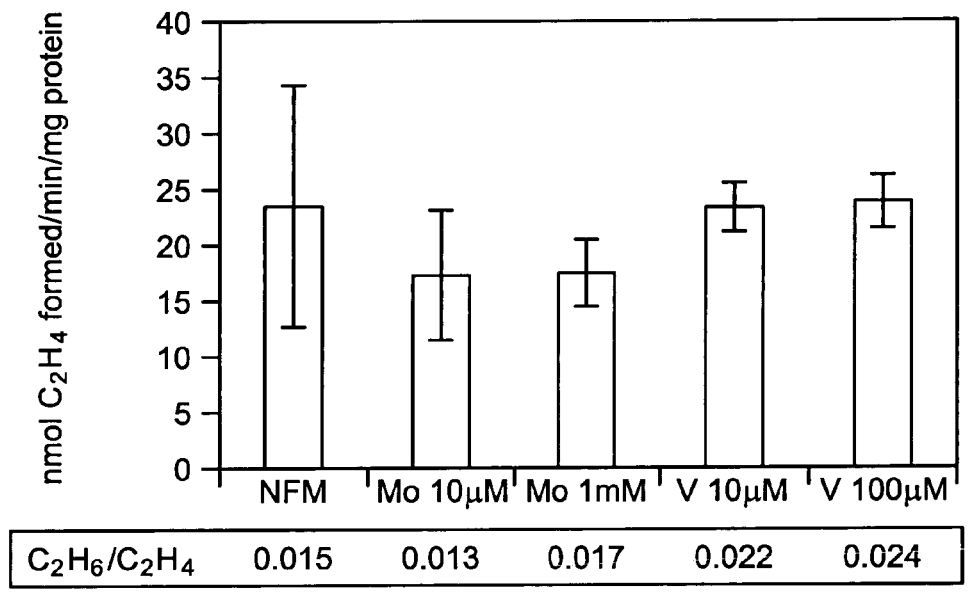
FIG. 9A illustrates the effect of molybdenum and vanadium on acetylene reduction activity of a ΔnifHΔanfH *R. palustris* strain grown in $N_2$-fixing medium (NFM). The concentration of molybdenum (Mo) and vanadium (V) in the medium is indicated. The $C_2H_6/C_2H_4$ ratio is also indicated. The nmol of $C_2H_4$ formed/minute/milligram of protein is indicated on the Y-axis.
Figure 9B:
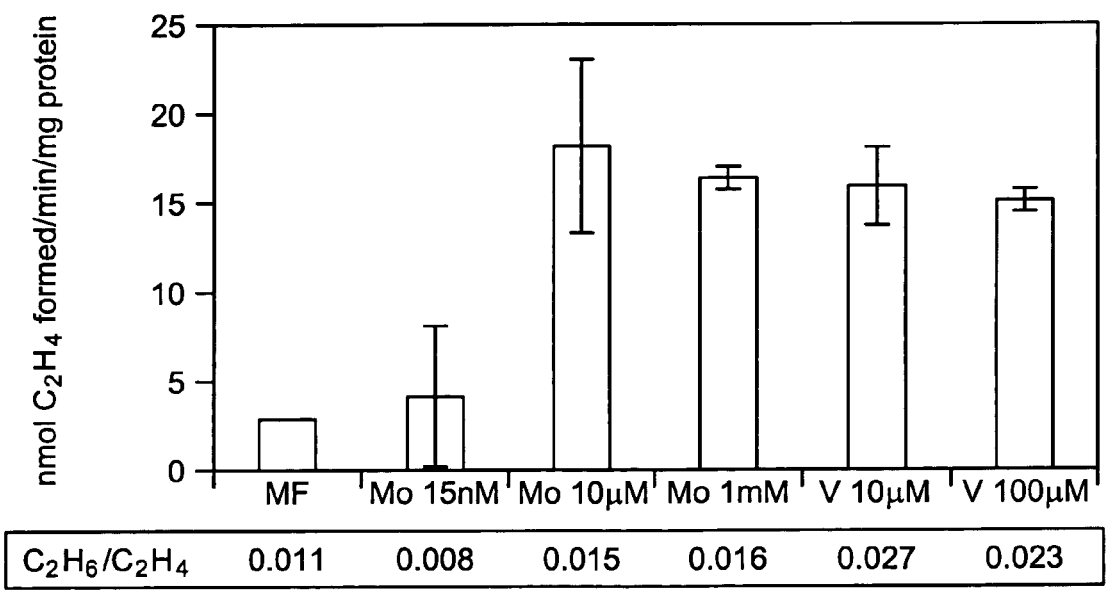
FIG. 9B illustrates the effect of molybdenum and vanadium on acetylene reduction activity of a ΔnifHΔanfH *R. palustris* strain grown in Mo/V-depleted medium (MF). The concentration of molybdenum (Mo) and vanadium (V) in the medium is indicated. The $C_2H_6/C_2H_4$ ratio is also indicated. The nmol of $C_2H_4$ formed/minute/milligram of protein is indicated on the Y-axis.

The ΔnifH ΔanfH mutant exhibited characteristics that are consistent with a strain that is synthesizing a hybrid VnfH-NifHDK enzyme. Rates of acetylene reduction by the ΔnifH ΔanfH strain were not altered by addition of molybdenum to concentrations as high as 1 mM (FIG. 9A). The relative amount of ethane produced in the standard nitrogen fixing growth medium by the ΔnifHΔanfH suggested a vanadium nitrogenase activity and further addition of vanadium did not stimulate rates of acetylene reduction by the ΔnifHΔanfH strain. However, the cells formed a slightly greater amount of ethane when grown in medium that was supplemented with vanadium. This information combined with the data from the ΔnifHnifD:Tn5 strain suggested that the ΔnifHΔanfH strain might be synthesizing an active nitrogenase that did not exist exclusively of VnfHGDK subunits. The addition of molybdenum to 8-hydroxyquinoline treated medium stimulated rates of acetylene reduction by the ΔnifHΔanfH strain. Vanadium addition also stimulated nitrogenase activity but the relative amount of ethane produced in the presence of vanadium was higher than that produced by the ΔnifHΔanfH strain grown with molybdenum only (FIG. 9B). The most direct explanation for these results is that the ΔnifHΔanfH mutant can synthesize not only a VnfHGDK but also a hybrid Vnf-HNifHDK enzyme. When cells are starved for vanadium, the activity of a hybrid VnfHNifHDK enzyme predominates.

Growth under nitrogen fixing conditions and nitrogenase activity of whole cell *R. palustris* wild-type and mutant strains is presented in Tables 7 and 8 below.

TABLE 7

| Strain | Genotype | Phenotype | Doubling time (hours) | Nitrogenase activity* |
|---|---|---|---|---|
| CGA009 | Wild-type | Wild-type | 9.8 ± 0.2 | 43.75 ± 2.07 |
| CGA753 | ΔnifH ΔanfH | Nif+ | 9.2 ± 0.2 | 50.20 ± 7.05 |
| CGA754 | ΔnifH ΔanfH | Vnf+ | 11.3 ± 0.7 | 11.01 ± 1.17 |
| CGA755 | ΔnifH ΔvnfH | Anf+ | 14.3 ± 0.8 | 1.22 ± 0.03 |
| CGA756 | ΔnifH ΔvnfH ΔanfH | None | No growth | ND** |

*Nitrogenase activity in nmol $C_2H_4$ formed/min/mg protein. Means and standard deviations are for at least triplicate cultures.
**ND, not determined.

TABLE 8

| Strain | $C_2H_6$ formation from $C_2H_2$ | $C_2H_6/C_2H_4$ | $H_2$ production* |
|---|---|---|---|
| CGA009 | No | ND | 52 ± 14 |
| CGA753 | No | ND | 54 ± 13 |
| CGA754 | Yes | 0.011 ± 0.003 | 117 ± 10 |
| CGA755 | Yes | 0.056 ± 0.004 | 245 ± 27 |
| CGA756 | ND | ND | ND |

*Hydrogen production in μmol/mg protein.

Example 4

Characterization of a Hydrogen Uptake Mutant

*R. palustris* strain CGA009 has a frameshift in the uptake hydrogenase regulatory system. A regulatory multicomponent system that modulates expression of the uptake hydrogenase in response to molecular $H_2$ has been characterized in other $H_2$ oxidizing bacteria (Lenz et al., J. Mol. Microbiol. Biotechnol., 4:255-262 (2002); Lenz and Friedrich, Proc. Natl. Acad. Sci. USA, 95:12474-12479 (1998); Elsen et al., J. Bacteriol., 178:5174-5181 (1996); Van Soom et al., Mol. Microbiol., 23:967-977 (1997)). This system consists of a $H_2$-sensor complex, known as a regulatory hydrogenase (RH) (Kleihues et al., J. Bacteriol., 182:2716-2724 (2000)) and a histidine protein kinase, which interacts with a response regulator protein (Lenz and Friedrich, Proc. Natl. Acad. Sci. USA, 95:12474-12479 (1998); Lenz et al., J. Mol. Microbiol. Biotechnol., 4:255-262 (2002); Richaud et al., J. Bacteriol., 173: 5928-5932 (1991); Elsen et al., J. Bacteriol., 179:968-971 (1997)). Specifically in *Ralstonia eutropha* the presence of $H_2$ inhibits the histidine kinase. This results in a dephosphorylated response regulator that activates transcription of the uptake hydrogenase genes. In the absence of $H_2$, the histidine kinase phosphorylates the response regulator (Lenz and Friedrich, Proc. Natl. Acad. Sci. USA, 95:12474-12479 (1998)). The phosphorylated response regulator is unable to activate gene expression (Dischert et al., Mol. Microbiol., 34:995-1006 (1999); Lenz and Friedrich, Proc. Natl. Acad. Sci. USA, 95:12474-12479 (1998)). Counterparts of these proteins are present in *R. palustris*; hupU (rpa0959) and hupV (rpa0960) encode for the regulatory hydrogenase subunits, hoxJ (rpa0980) encodes for the histidine kinase, and hoxA (rpa0979) encodes for the response regulator. Inspection of the genome revealed that *R. palustris* strain CGA009 has a frameshift in hupV. A 250 bp fragment containing the frameshift region of the hupV gene from strain CGA009 and five different *R. palustris* strains isolated from the environment were PCR amplified and sequenced. Alignment of these sequences revealed a four-base pair deletion in the hupV gene from strain CGA009. Using this information, hupV in strain CGA009 was repaired to generate strain CGA010.

Figure 10:
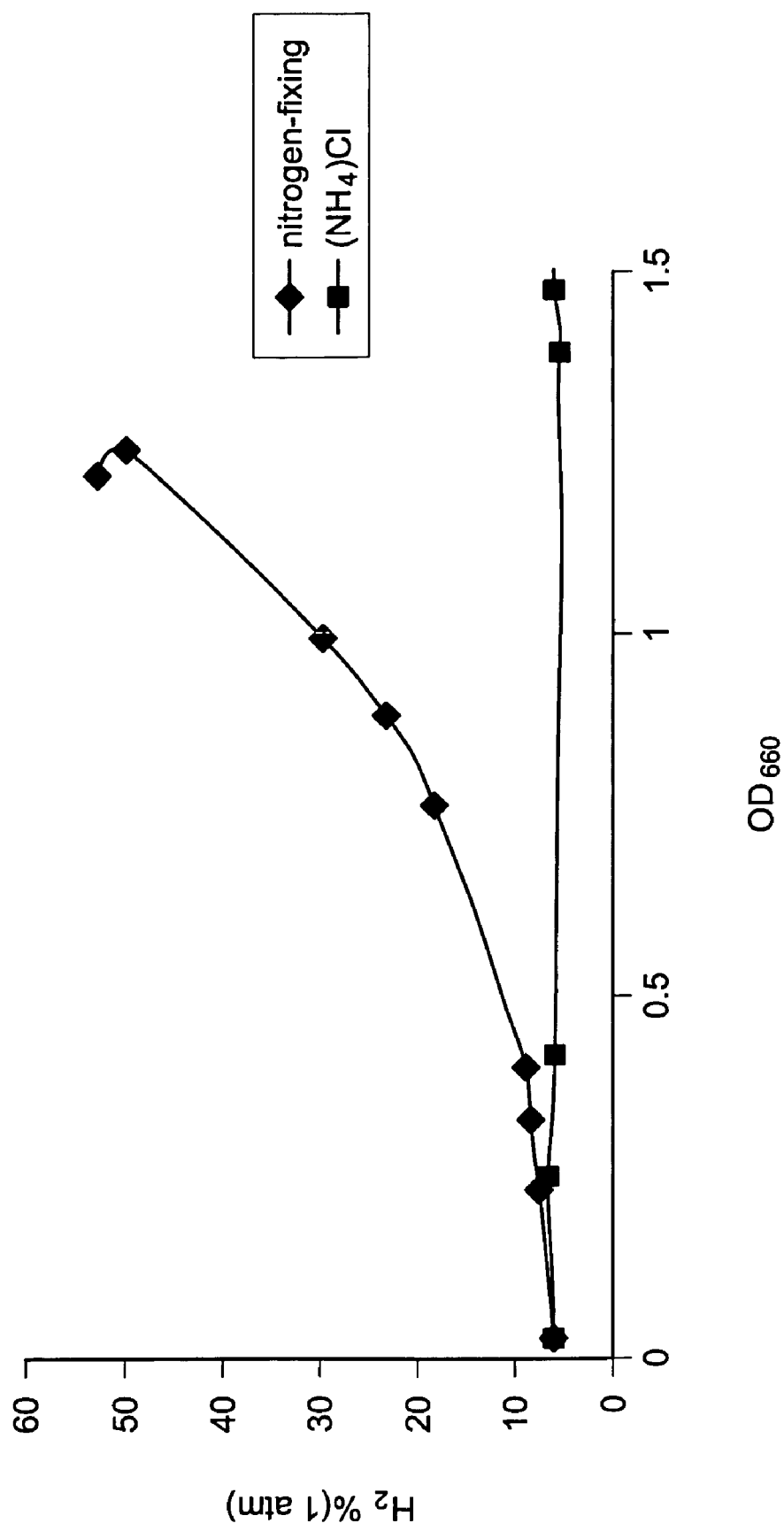
FIG. 10 illustrates $H_2$ production by a 10 milliliter culture of *R. palustris* strain CGA009 growing under $N_2$-fixing conditions. The optical density of the culture at 600 nm is indicated on the X-axis. $H_2$ production is indicated on the Y-axis as the percentage of the atmosphere in the headspace of the culture at 1 atmosphere (atm) of pressure. The line that includes diamonds indicates $H_2$ production by cells grown in nitrogen-fixing media. The line that includes squares indicates $H_2$ production by cells grown in $(NH_4)Cl$ containing media.

*R. palustris* strain CGA009 generates $H_2$ from plant-derived material under nitrogen-fixing conditions. Many studies have demonstrated that purple non-sulfur bacteria generate $H_2$ under nitrogen-fixing conditions (Barbosa et al., J. Biotechnol., 85:25-33 (2001); Hilmer and Gest, J. Bacteriol., 129:724-731 (1977); Mao et al., J. Ferment. Technol., 64:245-249 (1986)). *R. palustris* is, however, one of the few species in this group that can degrade plant lignin monomers and other aromatic compounds (Sasikala and Ramana, Adv. Microb. Physiol., 39:339-377 (1998)). $H_2$ production by *R. palustris* strain CGA009 growing under nitrogen-fixing conditions (10 ml cultures) was measured using p-coumarate (lignin monomer) as the carbon source and electron donor. The hydrogen accumulation in the headspace (17 ml) of a culture tube was equivalent to 60% in a gas mixture at 1 atmosphere (FIG. 10). Cultures supplied with ammonium, a nitrogen source that represses nitrogenase synthesis, did not produce $H_2$. This demonstrates the novel ability of *R. palustris* to derive electrons from green plant-derived material for $H_2$ production using only light as the energy source. *R. palustris* strain CGA009 is also able to utilize different carbon sources for the production of hydrogen.

TABLE 9

Hydrogen levels* produced by the *R. palustris* strains CGA009 (hupV), CGA010 (hupV+) and CGA550 (hupS)**

| Carbon Source (concentration) | CGA009 | CGA010 | CGA550 |
|---|---|---|---|
| Malate (10 mM) | 117 +/− 17 | Not detected | 111 +/− 42 |
| Succinate (10 mM) | 142 +/− 45 | 25 +/− 34 | 125 +/− 2 |
| Acetate (20 mM) | 205 +/− 45 | 111 +/− 60 | 214 +/− 24 |
| Benzoate (5.7 mM) | 211 +/− 25 | 44 +/− 22 | 217 +/− 19 |
| Cyclohexanecarboxylate (5.7 mM) | 242 +/− 19 | 36 +/− 9 | 274 +/− 14 |

*μmol hydrogen produced/milligram protein
**Data were acquired during stationary stage. Date represent the average of duplicates from three different experiments.

The complete disclosures of all patents, patent applications, publications, and nucleic acid and protein database entries, including for example GenBank accession numbers and EMBL accession numbers, that are cited herein are hereby incorporated by reference as if individually incorporated. Various modifications and alterations of this invention will become apparent to those skilled in the art without departing from the scope and spirit of this invention, and it should be understood that this invention is not to be unduly limited to the illustrative embodiments set forth herein.

What is claimed is:

1. A composite biological device comprising:
a layered biostructure comprising a first phototrophic biological material embedded in a first polymer layer, a second phototrophic biological material embedded in a second polymer layer, and at least one additional porous layer that does not contain a phototrophic biological material,
wherein each of the first phototrophic biological material and the second phototrophic biological material are metabolically active under non-growth conditions for at least 8 hours; and
wherein each of the first phototrophic biological material and the second phototrophic biological material can produce $H_2$ gas.

2. The device of claim 1, wherein at least one of the phototrophic biological materials can produce electricity.

3. The device of claim 1 wherein at least one of the phototrophic biological materials is thermotolerant.

4. The device of claim 1, wherein at least one of the phototrophic biological materials is aerobic or anaerobic.

5. The device of claim 1, wherein at least one of the phototrophic biological materials is genetically optimized for at least one of: light absorption and $H_2$ gas production.

6. The device of claim 1, wherein at least one of the phototrophic biological materials is a microorganism.

7. The device of claim 1, wherein at least one of the phototrophic biological materials *Rhodopseudomonas palustris*.

8. The device of claim 1, wherein at least one of the phototrophic biological materials comprises *Rhodopseudomonas palustris* with at least one mutated nitrogenase enzyme that results in increased $H_2$ gas evolution relative to the wild type organism.

9. The device of claim 8, wherein the *Rhodopseudomonas palustris* lacks a functional molybdenum nitrogenase, a functional iron nitrogenase, a functional vanadium nitrogenase, or any combination thereof.

10. The device of claim 9, wherein the *Rhodopseudomonas palustris* is a deletion mutant.

11. The device of claim 10, wherein the *Rhodopseudomonas palustris* deletion mutant is a ΔvnfH deletion mutant, a ΔanfH deletion mutant, a ΔnifH deletion mutant, a ΔvnfH-ΔanfH deletion mutant, a ΔnifHΔanfH deletion mutant, or a ΔnifHΔvnfH deletion mutant.

12. The device of claim 1, wherein at least one of the phototrophic biological materials comprises algae.

13. The device of claim 12, wherein the algae is *Chlamydomonas*.

14. The device of claim 1, wherein at least one of the layers is a light transmissive layer.

15. The device of claim 14, wherein the light transmissive layer is the polymer layer.

16. The device claim 1 wherein at least a portion of the biostructure comprises a nonporous latex-derived material.

17. The device of claim 1 wherein the biostructure comprises at least one layer comprising a porous latex-derived material and at least one layer comprising a nonporous latex-derived material.

18. The device of claim 17 wherein the nonporous latex-derived material defines at least one channel or at least one well.

19. The device of claim 1 wherein the polymer comprises an acrylate/vinyl acetate, polystyrene, or a polymer blend latex.

20. The device of claim 1 further comprising one or more carbohydrates.

21. The device of claim 1 wherein the biostructure forms a coating on a reflective substrate.

22. The device of claim 1 wherein the biostructure forms a coating on a conductive substrate.

23. The device of claim 1 wherein the biostructure forms a coating on a photosensitive substrate.

24. The device of claim 14 wherein the at least one light transmissive layer is conductive.

25. The device of claim 1 wherein the biostructure further comprises a spacer or channel layer.

26. The device of claim 25 wherein the spacer or channel layer is conductive.

27. A method of making a composite biological device, the method comprising:
depositing at least one first polymer layer comprising a first phototrophic biological material embedded in the first polymer layer onto a first porous layer that does not contain a phototrophic biological material to form a first biological material containing surface, and
depositing at least one second polymer layer comprising a second phototrophic biological material embedded in the second polymer layer onto a second porous layer that does not contain a phototrophic biological material to form a second biostructure having a biological material containing surface,
wherein the first polymer layer establishes non-growth conditions for the first phototrophic biological material and the second polymer layer establishes non-growth conditions for the second phototrophic biological material,
wherein each of the first phototrophic biological material and the second phototrophic biological material is metabolically active under the non-growth condition for at least 8 hours, and
wherein each of the first phototrophic biological material and the second phototrophic biological material can produce $H_2$ gas.

28. The method of claim 27, further comprising depositing at least one additional layer of a polymer on at least one of the phototrophic biological material containing surfaces of the device.

29. The method of claim 27, wherein the polymer comprises an acrylate/vinyl acetate, polystyrene, or a polymer blend latex.

30. The method of claim 28, wherein the polymer comprises an acrylate/vinyl acetate, polystyrene, or a polymer blend latex.

31. The method of claim 27, wherein the first layer is porous.

32. The method of claim 28, wherein the additional layer is porous.

33. The method of claim 27, wherein at least one of the phototrophic biological materials is aerobic or anaerobic.

34. The method of claim 27, wherein at least one of the phototrophic biological materials produces a gas in response to light.

35. The method of claim 27, wherein the gas is $H_2$ gas or carbon dioxide.

36. The method of claim 27, wherein at least one of the phototrophic biological materials is a metabolically active microorganism.

37. The method of claim 27, wherein at least one of the phototrophic biological materials comprises *Rhodopseudomonas palustris, Chlamydomonas, Rhodobacter, Rhodococcus, Geobacter*, a photosynthetic cyanobacterium, or any combination thereof.

38. The device of claim 1, wherein the first biological material and the second biological material are different.

39. A composite biological device comprising:
a layered biostructure comprising a polymer layer comprising a first phototrophic biological material and a second phototrophic biological material embedded in the polymer layer, and at least one additional porous layer that does not contain a phototrophic biological material,
wherein each of the first biological material and the second biological material is metabolically active under non-growth conditions for at least 8 hours; and
wherein each of the first phototrophic biological material and the second phototrophic biological material can produce $H_2$ gas.

40. The device of claim 39 wherein at least one of the phototrophic biological materials can produce electricity.

41. The device of claim 39 wherein at least one of the phototrophic biological materials is thermotolerant.

42. The device of claim 39, wherein at least one of the phototrophic biological materials is aerobic or anaerobic.

43. The device of claim 39, wherein at least one of the phototrophic biological materials is genetically optimized for at least one of: light absorption and $H_2$ gas production.

44. The device of claim 39, wherein at least one of the phototrophic biological materials is a microorganism.

45. The device of claim 39, wherein at least one of the phototrophic biological material comprises *Rhodopseudomonas palustris*, *Chlamydomonas*, *Rhodobacter*, *Rhodococcus*, *Geobacter*, a photosynthetic cyanobacterium, or any combination thereof.

46. The device of claim 39, wherein at least one of the phototrophic biological materials comprises *Rhodopseudomonas palustris* with at least one mutated nitrogenase enzyme that results in increased $H_2$ gas evolution relative to the wild type organism.

47. The device of claim 39, wherein at least one of the phototrophic biological materials comprises algae.

48. The device of claim 47, wherein the algae is *Chlamydomonas*.

49. The device of claim 39 wherein the biostructure forms a coating on a reflective substrate.

50. The device of claim 39 wherein the biostructure forms a coating on a conductive substrate.

51. The device of claim 39 wherein the biostructure forms a coating on a photosensitive substrate.

52. A method of making a composite biological device, the method comprising:
depositing at least one polymer layer comprising a first phototrophic biological material and a second phototrophic biological material embedded in the polymer layer onto a first porous layer that does not contain a phototrophic biological material,
wherein the polymer layer establishes non-growth conditions for the first phototrophic biological material and the second phototrophic biological material,
wherein each of the first phototrophic biological material and the second phototrophic biological material is metabolically active under the non-growth condition for at least 8 hours, and
wherein each of the first phototrophic biological material and the second phototrophic biological material can produce $H_2$ gas.

53. The method of claim 52, further comprising depositing at least one additional layer of a polymer on at least one of the phototrophic biological material containing surfaces of the device.

54. The method of claim 52, wherein at least one of the phototrophic biological materials is aerobic or anaerobic.

55. The method of claim 52, wherein at least one of the phototrophic biological materials produces a gas in response to light.

56. The method of claim 52, wherein the gas is $H_2$ gas or carbon dioxide.

57. The method of claim 52, wherein at least one of the phototrophic biological materials is a metabolically active microorganism.

58. The method of claim 52, wherein at least one of the phototrophic biological materials comprises *Rhodopseudomonas plaustris*, *Chlamydomonas*, *Rhodobacter*, *Rhodococcus*, *Geobacter*, a photosynthetic cyanobacterium, or any combination thereof.

59. A composite biological device comprising:
a layered biostructure comprising a first phototrophic biological material embedded in a first polymer layer, a second phototrophic biological material embedded in a second polymer layer, and at least one additional porous layer that does not contain a phototrophic biological material,
wherein each of the first phototrophic biological material and the second phototrophic biological material are metabolically active under non-growth conditions.

60. The composite biological device of claim 59, wherein at least one of the phototrophic biological materials comprises *Rhodopseudomonas plaustris*, *Chlamydomonas*, *Rhodobacter*, *Rhodococcus*, *Geobacter*, a photosynthetic cyanobacterium, or any combination thereof.

61. The composite biological device of claim 1, wherein at least one of the phototrophic biological materials comprises *Rhodopseudomonas plaustris*, *Chlamydomonas*, *Rhodobacter*, *Rhodococcus*, *Geobacter*, a photosynthetic cyanobacterium, or any combination thereof.

* * * * *

UNITED STATES PATENT AND TRADEMARK OFFICE
CERTIFICATE OF CORRECTION

PATENT NO. : 7,745,023 B2  
APPLICATION NO. : 10/915934  
DATED : June 29, 2010  
INVENTOR(S) : Flickinger et al.

Page 1 of 1

It is certified that error appears in the above-identified patent and that said Letters Patent is hereby corrected as shown below:

Title Page, Item (73) Assignee, add:

--University of Iowa Research Foundation  
Iowa City, Iowa (US)--.

Signed and Sealed this

Tenth Day of August, 2010

David J. Kappos  
*Director of the United States Patent and Trademark Office*